(12) United States Patent
Karaborni

(10) Patent No.: US 11,008,321 B2
(45) Date of Patent: May 18, 2021

(54) CRYSTALLINE FORM OF AN AVIBACTAM DERIVATIVE

(71) Applicant: ARIXA PHARMACEUTICALS, INC., Palo Alto, CA (US)

(72) Inventor: Sami Karaborni, Cupertino, CA (US)

(73) Assignee: Arixa Pharmaceuticals, Inc., New York, NY (US)

( * ) Notice: Subject to any disclaimer, the term of this patent is extended or adjusted under 35 U.S.C. 154(b) by 0 days.

(21) Appl. No.: 16/813,930

(22) Filed: Mar. 10, 2020

(65) Prior Publication Data
US 2020/0291022 A1 Sep. 17, 2020

Related U.S. Application Data

(60) Provisional application No. 62/817,243, filed on Mar. 12, 2019.

(51) Int. Cl.
| | | |
|---|---|---|
| C07D 471/08 | (2006.01) | |
| A61K 9/00 | (2006.01) | |
| A61K 31/551 | (2006.01) | |
| A61K 45/06 | (2006.01) | |

(52) U.S. Cl.
CPC .......... *C07D 471/08* (2013.01); *A61K 9/0053* (2013.01); *A61K 45/06* (2013.01); *C07B 2200/13* (2013.01)

(58) Field of Classification Search
CPC .......................... C07D 471/08; A61K 31/551
See application file for complete search history.

(56) References Cited

U.S. PATENT DOCUMENTS

| | | | |
|---|---|---|---|
| 3,658,849 A | 4/1972 | Leffingwell | |
| 4,522,811 A | 6/1985 | Eppstein et al. | |
| 5,674,533 A | 10/1997 | Santus et al. | |
| 6,627,646 B2 * | 9/2003 | Bakale | A61P 37/08 514/322 |
| 7,112,592 B2 | 9/2006 | Lampilas et al. | |
| 7,994,218 B2 | 8/2011 | Jandeleit et al. | |
| 8,168,617 B2 | 5/2012 | Jandeleit et al. | |
| 8,772,490 B2 | 7/2014 | Abe et al. | |
| 9,035,062 B2 | 5/2015 | Abe et al. | |
| 9,284,273 B2 | 3/2016 | Abe et al. | |
| 9,340,493 B2 | 5/2016 | Brown et al. | |
| 9,393,239 B2 | 7/2016 | Maiti et al. | |
| 10,085,999 B1 * | 10/2018 | Gordon | A61P 31/04 |
| 2009/0099253 A1 | 4/2009 | Li et al. | |
| 2011/0294777 A1 | 12/2011 | Blizzard et al. | |
| 2014/0045943 A1 | 2/2014 | Khan et al. | |
| 2015/0196559 A1 | 7/2015 | Wang et al. | |
| 2015/0225335 A1 | 8/2015 | Takashima et al. | |
| 2017/0165371 A1 | 6/2017 | Goldberg | |
| 2017/0290918 A1 | 10/2017 | Honda et al. | |
| 2017/0296503 A1 | 10/2017 | Eto et al. | |
| 2018/0148448 A1 | 5/2018 | Wu | |

FOREIGN PATENT DOCUMENTS

| | | |
|---|---|---|
| DE | 3045373 | 7/1982 |
| RU | 2445314 | 4/2013 |
| WO | 2007/116922 | 10/2007 |
| WO | 2009/033054 | 3/2009 |
| WO | 2009/033079 | 3/2009 |
| WO | 2009/091856 | 7/2009 |
| WO | 2009/092606 | 7/2009 |
| WO | 2010/126820 | 11/2010 |
| WO | 2011/046771 | 4/2011 |
| WO | 2011/150380 | 12/2011 |
| WO | 2012/086241 | 6/2012 |
| WO | 2012/165648 | 12/2012 |
| WO | 2016/116788 | 7/2016 |
| WO | 2017/045510 | 3/2017 |
| WO | 2018/208557 A1 | 11/2018 |

OTHER PUBLICATIONS

CMU Pharmaceutical polymorphism, internet p. 1-3 printout Apr. 3, 2008. (Year: 2002).*
Singhal et al., "Drug Polymorphism, etc.," Advanced Drug Delivery reviews 56, p. 335-347. (Year: 2004).*
Concise Encyclopedia Chemistry, NY: Walter de Gruyter, 872-873. (Year: 1993).*
Jain et al., Polymorphism in Pharmacy, Indian Drugs, 23(6) 315-329. (Year: 1979).*
Muzaffar et al,, "Polymorphism and Drug, etc.," J of Pharm. (Lahore), 1(1), 59-66. (Year: 1979).*
U.S. Pharmacopia #23, National Formulary #18, 1843-1844. (Year: 1995).*
Doelker, english translation of S.T.P. Pratiques, 9(5), 399-409, pp. 1-33. (Year: 1999).*
Doelker, english translation of Ann. Pharm. Fr., 60: 161-176, pp. 1-39. (Year: 2002).*
Taday et al, "Using Terahertz, etc.," J of Pharm. Sci., 92(4), 831-838. (Year: 2003).*
Otuska et al., "Effect of Polymorphic, etc.," Chem. Pharm. Bull., 47(6) 852-856. (Year: 1999).*
Beaudoin et al., "Bioanalytical method validation for the simultaneous determination of ceftazidime and avibactam in rat plasma," Bioanalysis, 2016, vol. 8, No. 2, p. 111-122.
Beaudoin et al., "Preparation of Unsymmetrical Sulfonyureas from N,N-Sulfuryldiimidazoles," the Journal of Organic Chemistry, 2003, vol. 68, No. 1, p. 115-119.
Boyd et al., "NMR spectroscopic studies of intermediary metabolites of cyclophosphamide. 2. Direct observation, characterization, and reactivity studies of iminocyclophosphamide and related species," The Journal of Medicinal Chemistry, 1987, vol. 30, No. 2, p. 366-374.
DeBergh et al., "Synthesis of Aryl Sulfonamides via Palladium-Catalyzed Chlorosulfonylation of Arylboronic Acids," Journal of the American Chemical Society, 2013, vol. 135, No. 29, p. 10638-10641.
Hecker et al., "Discovery of a Cyclic Boronic Acid β-Lactamase Inhibitor (RPX7009) with Utility vs Class A Serine Carbapenemases," Journal of Medicinal Chemistry, 2015, vol. 58, p. 3682-3692.

(Continued)

*Primary Examiner* — Patricia L Morris
(74) *Attorney, Agent, or Firm* — Jason G. Tebbutt

(57) ABSTRACT

A crystalline form of an avibactam derivative, pharmaceutical compositions thereof, and the use of the crystalline avibactam derivative for treating bacterial infections are provided.

12 Claims, 6 Drawing Sheets

(56) References Cited

OTHER PUBLICATIONS

Illa et al., "Practical and Highly Selective Sulfur Ylide-Mediated Asymmetric Expoxidations and Aziridinations Using a Cheap and Readily Available Chiral Sulfide: Extensive Studies to Map Out Scope, Limitations, and Rationalization of Diastereo- and Enantioselectivities," Journal of the American Chemical Society, 2013, vol. 135, No. 32, p. 11951-11966.
King et al., "Structural and Kinetic Characterization of Diazabicyclooctanes as Dual Inhibitors of Both Seratin-B-Lactamase and Penicillin-Binding Proteins," ACS Chemical Biology, 2016, vol. 11, No. 4, p. 864-868.
Oger et al., "Lipase-Catalyzed Regioselective Monoacetylation of Unsymmetrical 1,5-Primary Diols," The Journal of Organic Chemistry, 2010, vol. 75, No. 6, p. 1892-1897.
Levasseur et al., "In vitro antibacterial activity of the ceftazidime-avibactam combination against enterobacteriaceae, including strains with well-characterized β-lactamases," Antimicrobial Agents Chemotherapy, 2015, vol. 59, No. 4, p. 1931-1634.
Livermore et al., "Activity of OP0595/β-lactam combinations against Gram-negative bacteria with extended-spectrum, AmpC and carapenem—hydrolysing β-lactamases," Journal of Antimicrobial Chemotherapy, 2015, vol. 70, Issue 11, p. 3032-3041.
Rusha et al., "Design and application of esterase-labile sulfonate protecting groups," Chemical Communications, 2011, vol. 47, p. 2038-2040.
Shi et al., "The Rhodium-Catalyzed Carbene Cyclization Cycloaddition Cascade Reaction of Vinylsulfonates," Advanced Synthesis and Catalysis, 2009, vol. 351, p. 3128-3132.
Simpson et al., "A Comprehensive Approach to the Synthesis of Sulfate Esters," Journal of the American Chemical Society, 2006, vol. 128, No. 5, p. 1605-1610.
Soengas et al., "Convenient Procedure for the Indium-Mediated Hydroxymethylation of Active Bromo Compounds: Transformation of Ketones into a-Hydroxymethyl Nitroalkanes," Synlett, 2010, vol. 17, p. 2625-2627.
Zasowski et al., "The β-Lactams Strike Back: Ceftazidime-Avibactam," Pharmacotherapy, 2015, vol. 35, Issue 8, p. 755-770.
Zhang et al., "Enhanced Photoresponsive Ultrathin Graphitic-Phase C3N4 Nanosheets for Bioimaging," Journal of the American Chemical Society, 2013, vol. 135, No. 1, p. 18-21.
International Search Report and Written Opinion for Application No. PCT/US2018/030652, dated Aug. 29, 2018, 13 pages.
International Search Report and Written Opinion for Application No. PCT/US2019/053990, dated Dec. 4, 2019, 14 pages.
Caira, M., "Crystalline Polymorphism of Organic Compounds", Topics in Current Chemistry, 1998, vol. 198, p. 163-208.
Gordon et al., "Orally Absorbed Derivatives of the [beta]-Lactamase Inhibitor Avibactam. Design of Novel Prodrugs of Sulfate Containing Drugs." Journal of Medicinal Chemistry, 2018, vol. 61, No. 22, p. 10340-10344.
International Search Report and Written Opinion for Application No. PCT/US2020/021795, dated May 20, 2020, 15 pages.
Search Report for Russia Application No. 2019135891, dated Feb. 6, 2020, 2 pages.
Abdelraouf et al., "In Vivo Pharmacodynamic Profile of Ceftibuten/Clavulanate Combination against Extended Spectrum Beta-lactamase-Producing Enterobacteriaceae in the Murine Thigh Infection Model", Antimicrobial Agents and Chemotherapy, May 6, 2019, 34 pages.
Grupper et al., "In Vitro Pharmacodynamics of a Novel Ceftibuten-Clavulanate Combination Antibiotic against Enterobacteriaceae", Antimicrobial Agents and Chemotherapy, May 6, 2019, 33 pages.
Merdjan et al., "Safety, Single Dose Pharmacokinetics, and Pharmacodynamics of Beta-Lactamase Inhibitor NXL104 in Healthy Young Male Adults", 47th Interscience Conference on Antimicrobial Agents and Chemotherapy, 2007, 1 page.
Merdjan et al., "Safety and Pharmacokinetics of Single and Multiple Ascending Doses of Avibactam Alone and in Combination with Ceftazidime in Healthy Male Volunteers: Results of Two Randomized, Placebo-Controlled Studies", Clinical Drug Investigation, Mar. 2015, 11 pages.
VanScoy B. D., A. Mullarkey, H. Conde, N. Onufrak, J. Trias, C. Sable, S. M. Bhavnani, P. G. Ambrose. Evaluation of the Pharmacokinetics-Pharmacodynamics of Oral Avibactam in Combination with Ceftibuten Using a One-Compartment In Vitro Infection Model. Abstract T-07, 2019 ASM/ESCMID Conference on Drug Development to Meet the Challenge of Antimicrobial Resistance, Boston, Massachusetts Presented on Thursday Sep. 5, 2019.

* cited by examiner

1

CRYSTALLINE FORM OF AN AVIBACTAM DERIVATIVE

This application claims the benefit under 35 U.S.C. § 119(e) of U.S. Provisional Application No. 62/817,243, filed on Mar. 12, 2019, which is incorporated by reference in its entirety.

FIELD

The present disclosure relates to a crystalline form of an avibactam derivative, pharmaceutical compositions thereof, and the use of the crystalline avibactam derivative for treating bacterial infections.

BACKGROUND

Overuse, incorrect use, and agricultural use of antibiotics has led to the emergence of resistant bacteria that are refractory to eradication by conventional anti-infective agents such as those based on β-lactams or fluoroquinolone architectures. Alarmingly, many of these resistant bacteria are responsible for common infections including, for example, pneumonia, sepsis, and others.

Development of resistance to commonly used β-lactam anti-infectives is related to expression of β-lactamases by the targeted bacteria. β-Lactamases typically hydrolyze the β-lactam ring, thus rendering the antibiotic ineffective against the bacteria. Accordingly, inhibition of β-lactamases by a suitable substrate can prevent degradation of the β-lactam antibiotic, thereby increasing the effectiveness of the administered antibiotic and mitigating the emergence of resistance.

Avibactam is a known β-lactamase inhibitor that is currently marketed in combination with ceftazidime to treat gram negative bacterial infections. Avibactam must be administered intravenously, which limits use to expensive clinical settings.

SUMMARY

According to the present invention, crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate is characterized by an X-ray powder diffraction (XRPD) pattern having characteristic scattering angles (2θ) at least at 3.16°±0.2°, 6.37°±0.2°, 5.38°±2°, and 17.35°±0.2° at a Kα2/Kα1 (0.5) wavelength.

According to the present invention, methods of preparing crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate (1) anhydrate comprise dissolving ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate in a mixture of ethyl acetate, water, and n-heptane to form a triphasic mixture; and precipitating crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate from the triphasic mixture.

BRIEF DESCRIPTION OF THE DRAWINGS

Those skilled in the art will understand that the drawings described herein are for illustration purposes only. The drawings are not intended to limit the scope of the present disclosure.

DETAILED DESCRIPTION

Figure 1:
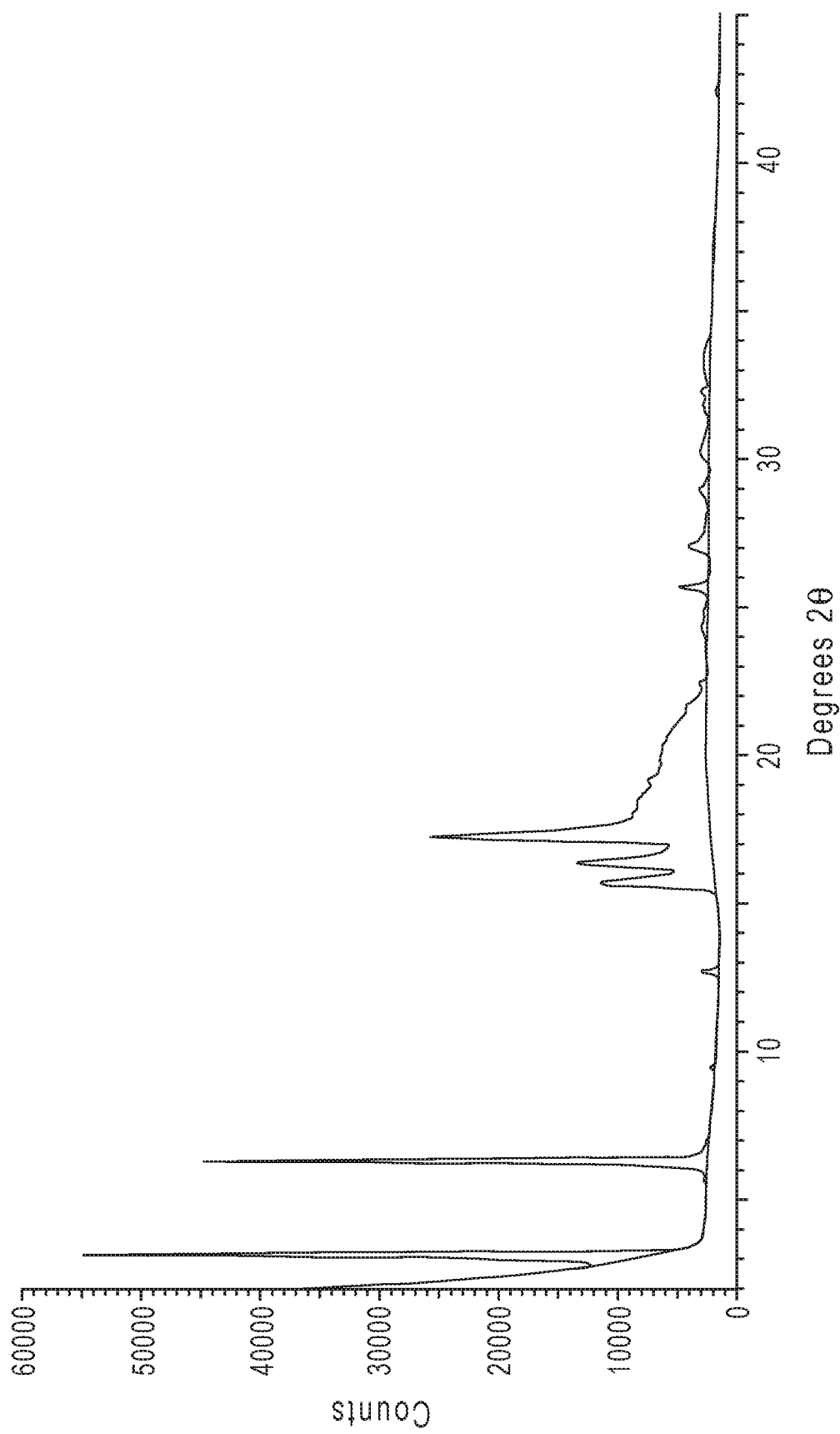
FIG. 1 shows an X-ray powder diffraction (XRPD) pattern of crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1).

A dash ("-") that is not between two letters or symbols is used to indicate a point of attachment for a moiety or substituent. For example, —CONH$_2$ is attached through the carbon atom.

"Alkyl" refers to a saturated, branched, or straight-chain, monovalent hydrocarbon radical derived by the removal of one hydrogen atom from a single carbon atom of a parent alkane, alkene, or alkyne. An alkyl group can be, for example, $C_{1-10}$ alkyl, $C_{1-6}$ alkyl, $C_{1-5}$ alkyl, $C_{1-4}$ alkyl, or $C_{1-3}$ alkyl. An alkyl can be, for example, methyl, ethyl, n-propyl, iso-propyl, n-butyl, tert-butyl or iso-butyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, $C_{1-4}$ alkoxy, $C_{1-3}$ alkoxy, ethoxy, or methoxy.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms selected from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like. An aryl group can be $C_{6-10}$ aryl, $C_{6-9}$ aryl, $C_{6-8}$ aryl, or phenyl. Aryl, however, does not encompass or overlap in any way with heteroaryl, separately defined herein.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl. Where specific alkyl moieties are intended, the nomenclature arylalkanyl, arylalkenyl, or arylalkynyl is used. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-16}$ arylalkyl, such as the alkanyl, alkenyl or alkynyl moiety of the arylalkyl group is $C_{1-6}$ and the aryl moiety is $C_{6-10}$. An arylalkyl group can be $C_{7-9}$ arylalkyl, wherein the alkyl moiety can be $C_{1-3}$ alkyl and the aryl moiety can be phenyl. An arylalkyl group can be $C_{7-16}$ arylalkyl, $C_{7-14}$ arylalkyl, $C_{7-12}$ arylalkyl, $C_{7-10}$ arylalkyl, $C_{7-8}$ arylalkyl, or benzyl.

"Avibactam derivative" refers to an avibactam derivative of Formula (1), a pharmaceutically acceptable salt thereof, a hydrate thereof, a solvate thereof, or a combination of any of the forgoing. An avibactam derivative of Formula (1) includes sub-genuses and specific compounds within the scope of Formula (1). When orally administered, an avibactam derivative provides avibactam in the plasma of a patient.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to maximum concentration ($C_{max}$) of a drug in the plasma or blood of a patient following administration of a dose of the drug or form of drug to the patient.

"Oral bioavailability" (F %) refers to the fraction of an oral administered drug that reaches systemic circulation. Oral bioavailability is a product of the fraction absorbed, the fraction escaping gut-wall elimination, and the fraction escaping hepatic elimination; and the factors that influence bioavailability can be divided into physiological, physicochemical, and biopharmaceutical factors.

"Compounds" and moieties disclosed herein include any specific compounds within the disclosed formula. Compounds may be identified either by their chemical structure and/or chemical name. Compounds are named using the ChemBioDraw Ultra Version 14.0.0.117 (CambridgeSoft, Cambridge, Mass.) nomenclature/structure program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

"Cycloalkyl" refers to a saturated or partially unsaturated cyclic alkyl radical. A cycloalkyl group can be $C_{3-6}$ cycloalkyl, $C_{3-5}$ cycloalkyl, $C_{5-6}$ cycloalkyl, cyclopropyl, cyclopentyl, or cyclohexyl. A cycloalkyl can be selected from, for example, cyclopropyl, cyclobutyl, cyclopentyl, and cyclohexyl.

"Cycloalkylalkyl" refers to an acyclic alkyl radical in which one of the hydrogen atoms bonded to a carbon atom is replaced with a cycloalkyl group as defined herein. A cycloalkylalkyl group can be $C_{4-30}$ cycloalkylalkyl, for example, the alkyl moiety of the cycloalkylalkyl group is $C_{1-10}$ and the cycloalkyl moiety of the cycloalkylalkyl moiety is $C_{3-20}$. A cycloalkylalkyl group can be $C_{4-20}$ cycloalkylalkyl for example, the alkanyl, alkenyl, or alkynyl moiety of the cycloalkylalkyl group is $C_{1-8}$ and the cycloalkyl moiety of the cycloalkylalkyl group is $C_{3-12}$. A cycloalkylalkyl can be $C_{4-9}$ cycloalkylalkyl, wherein the alkyl moiety of the cycloalkylalkyl group is $C_{1-3}$ alkyl, and the cycloalkyl moiety of the cycloalkylalkyl group is $C_{3-6}$ cycloalkyl. A cycloalkylalkyl group can be $C_{4-12}$ cycloalkylalkyl, $C_{4-10}$ cycloalkylalkyl, $C_{4-8}$ cycloalkylalkyl, and $C_{4-6}$ cycloalkylalkyl. A cycloalkylalkyl group can be cyclopropylmethyl (—$CH_2$-cyclo-$C_3H_5$), cyclopentylmethyl (—$CH_2$-cyclo-$C_5H_9$), or cyclohexylmethyl (—$CH_2$-cyclo-$C_6H_{11}$). A cycloalkylalkyl group can be cyclopropylethenyl (—CH=CH-cyclo-$C_3H_5$), or cyclopentylethynyl (—C≡C-cyclo-$C_5H_9$).

"Cycloalkylheteroalkyl" by itself or as part of another substituent refers to a heteroalkyl group in which one or more of the carbon atoms (and certain associated hydrogen atoms) of an alkyl group are independently replaced with the same or different heteroatomic group or groups and in which one of the hydrogen atoms bonded to a carbon atom is replaced with a cycloalkyl group. In a cycloalkylheteroalkyl, the heteroatomic group can be selected from —O—, —S—, —NH—, —N(—$CH_3$)—, —SO—, and —$SO_2$—, or the heteroatomic group can be selected from —O— and —NH—, or the heteroatomic group is —O— or —NH—.

"Cycloalkyloxy" refers to a radical —OR where R is cycloalkyl as defined herein. Examples of cycloalkyloxy groups include cyclopropyloxy, cyclobutyloxy, cyclopentyloxy, and cyclohexyloxy. A cycloalkyloxy group can be $C_{3-6}$ cycloalkyloxy, $C_{3-5}$ cycloalkyloxy, $C_{5-6}$ cycloalkyloxy, cyclopropyloxy, cyclobutyloxy, cyclopentyloxy, or cyclohexyloxy.

"Disease" refers to a disease, disorder, condition, or symptom of any of the foregoing.

"Heteroalkoxy" refers to an alkoxy group in which one or more of the carbon atoms are replaced with a heteroatom. A heteroalkoxy group can be, for example, $C_{1-6}$ heteroalkoxy, $C_{1-5}$ heteroalkoxy, $C_{1-4}$ heteroalkoxy, or $C_{1-3}$ heteroalkoxy. In a heteroalkoxy, the heteroatomic group can be selected from —O—, —S—, —NH—, —NR—, —$SO_2$—, and —$SO_2$—, or the heteroatomic group can be selected from —O— and —NH—, or the heteroatomic group is —O— and —NH—. A heteroalkoxy group can be $C_{1-6}$ heteroalkoxy, $C_{1-5}$ heteroalkoxy, $C_{1-4}$ heteroalkoxy, or $C_{1-3}$ heteroalkoxy.

"Heteroalkyl" by itself or as part of another substituent refer to an alkyl group in which one or more of the carbon atoms (and certain associated hydrogen atoms) are independently replaced with the same or different heteroatomic group or groups. Examples of heteroatomic groups include —O—, —S—, —NH—, —NR—, —O—O—, —S—S—, =N—N=, —N=N—, —N=N—NR—, —PR—, —P(O)OR—, —P(O)R—, —POR—, —SO—, —SO$_2$—, —Sn(R)$_2$—, and the like, where each R can independently be selected from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, and substituted $C_{7-18}$ heteroarylalkyl. Each R in a heteroatomic group can be independently selected from hydrogen and $C_{1-3}$ alkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example, $C_{1-6}$ heteroalkyl includes groups having five carbon atoms and one heteroatom, groups having four carbon atoms and two heteroatoms, and so forth. In a heteroalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—. A heteroalkyl group can be $C_{1-6}$ heteroalkyl, $C_{1-5}$ heteroalkyl, or $C_{1-4}$ heteroalkyl, or $C_{1-3}$ heteroalkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. When the total number of N, S, and O atoms in the heteroaryl group exceeds one, the heteroatoms may or may not be adjacent to one another. The total number of heteroatoms in the heteroaryl group is not more than two. In a heteroaryl, the heteroatomic group can be selected from —O—, —S—, —NH—, —N(—CH$_3$)—, —S(O)—, and —SO$_2$—, or the heteroatomic group can be selected from —O— and —NH—, or the heteroatomic group can be —O— or —NH—. A heteroaryl group can be selected from, for example, $C_{5-10}$ heteroaryl, $C_{5-9}$ heteroaryl, $C_{5-8}$ heteroaryl, $C_{5-7}$ heteroaryl, $C_{5-6}$ heteroaryl, $C_5$ heteroaryl, or $C_6$ heteroaryl.

Examples of suitable heteroaryl groups include groups derived from acridine, arsindole, carbazole, α-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, or oxazolidine. A heteroaryl group can be derived from thiophene, pyrrole, benzothiophene, benzofuran, indole, pyridine, quinoline, imidazole, oxazole, or pyrazine. For example, a heteroaryl can be $C_5$ heteroaryl and can be selected from furyl, thienyl, pyrrolyl, imidazolyl, pyrazolyl, isothiazolyl, or isoxazolyl. A heteroaryl can be $C_6$ heteroaryl, and can be selected from pyridinyl, pyrazinyl, pyrimidinyl, and pyridazinyl.

"Heteroarylalkyl" refers to an arylalkyl group in which one of the carbon atoms (and certain associated hydrogen atoms) is replaced with a heteroatom. A heteroarylalkyl group can be, for example, $C_{6-16}$ heteroarylalkyl, $C_{6-14}$ heteroarylalkyl, $C_{6-12}$ heteroarylalkyl, $C_{6-10}$ heteroarylalkyl, $C_{6-8}$ heteroarylalkyl, $C_7$ heteroarylalkyl, or $C_6$ heteroarylalkyl. In a heteroarylalkyl, the heteroatomic group can be selected from, for example, —O—, —S—, —NH—, —N(—CH$_3$)—, —SO—, and —SO$_2$—, or the heteroatomic group can be selected from —O— and —NH—, or the heteroatomic group can be —O— or —NH—.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system violates the Huckel-rule. Examples of heteroatoms to replace the carbon atom(s) include N, P, O, S, and Si. Examples of heterocycloalkyl groups include groups derived from epoxides, azirines, thiiranes, imidazolidine, morpholine, piperazine, piperidine, pyrazolidine, pyrrolidine, and quinuclidine. A heterocycloalkyl can be $C_5$ heterocycloalkyl and can be selected from pyrrolidinyl, tetrahydrofuranyl, tetrahydrothiophenyl, imidazolidinyl, oxazolidinyl, thiazolidinyl, doxolanyl, and dithiolanyl. A heterocycloalkyl can be $C_6$ heterocycloalkyl and can be selected from piperidinyl, tetrahydropyranyl, piperizinyl, oxazinyl, dithianyl, and dioxanyl. A heterocycloalkyl group can be $C_{3-6}$ heterocycloalkyl, $C_{3-5}$ heterocycloalkyl, $C_{5-6}$ heterocycloalkyl, $C_5$ heterocycloalkyl or $C_6$ heterocycloalkyl. In a heterocycloalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Heterocycloalkylalkyl" refers to a cycloalkylalkyl group in which one or more carbon atoms (and certain associated hydrogen atoms) of the cycloalkyl ring are independently replaced with the same or different heteroatom. A heterocycloalkylalkyl can be, for example, $C_{4-12}$ heterocycloalkylalkyl, $C_{4-10}$ heterocycloalkylalkyl, $C_{4-8}$ heterocycloalkylalkyl, $C_{4-6}$ heterocycloalkylalkyl, $C_{6-7}$ heterocycloalkylalkyl, or $C_6$ heterocycloalkylalkyl or $C_7$ heterocycloalkylalkyl. In a heterocycloalkylalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Hydrate" refers to a compound in which water is incorporated into the crystal lattice, in a stoichiometric proportion, resulting in the formation of an adduct. Methods of making hydrates include, for example, storage in an atmosphere containing water vapor, dosage forms that include water, or routine pharmaceutical processing steps such as, for example, crystallization such as from water or mixed aqueous solvents, lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. A compound can be, for example, a monohydrate, a dihydrate, or a trihydrate.

"Patient" refers to a mammal, for example, a human.

"Parent aromatic ring system" refers to an unsaturated cyclic or polycyclic ring system having a cyclic conjugated π (pi) electron system with 4n+2 electrons (Huickel rule). Included within the definition of "parent aromatic ring system" are fused ring systems in which one or more of the rings are aromatic and one or more of the rings are saturated or unsaturated, such as, for example, fluorene, indane, indene, or phenalene. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, and trinaphthalene.

"Parent aromatic ring system" refers to an unsaturated cyclic or polycyclic ring system having a conjugated π electron system. Included within the definition of "parent aromatic ring system" are fused ring systems in which one or more of the rings are aromatic and one or more of the rings are saturated or unsaturated, such as, for example, fluorene, indane, indene, and phenalene. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of π-electrons corresponding to the Hückel rule (4n+2). Examples of heteroatoms to replace the carbon atoms include N, P, O, S, and Si. Included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, and xanthene. Examples of parent heteroaromatic ring systems include arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (1) and at least one pharmaceutically acceptable vehicle, with which the compound of Formula (1) is administered to a patient. Pharmaceutically acceptable vehicles are known in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by taking the compound in a preventative fashion. The application of a therapeutic for preventing or prevention of a disease of disorder is known as prophylaxis.

"Prodrug" refers to a derivative of a drug molecule that requires a transformation within the body to release the active drug. Prodrugs are frequently, although not necessarily, pharmacologically inactive until converted to the parent drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature or pH. The agent may be endogenous to the conditions of use, such as an enzyme present in the systemic circulation of a patient to which the prodrug is administered or the acidic conditions of the stomach or the agent may be supplied exogenously. For example, for a compound of Formula (1), the promoiety can has the structure:

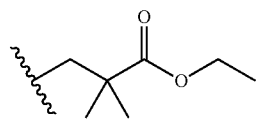

"Substituted" refers to a group in which one or more hydrogen atoms are independently replaced with the same or different substituent(s). Each substituent can be independently selected from deuterio, halogen, —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl. Each substituent can be independently selected from deuterio, halogen, —NH$_2$, —OH, C$_{1-3}$ alkoxy, and C$_{1-3}$ alkyl, trifluoromethoxy, and trifluoromethyl. Each substituent can be independently selected from, for example, deuterio, —OH, methyl, ethyl, trifluoromethyl, methoxy, ethoxy, and trifluoromethoxy. Each substituent can be selected from, for example, deuterio, C$_{1-3}$ alkyl, =O, C$_{1-3}$ alkyl, C$_{1-3}$ alkoxy, and phenyl. Each substituent can be selected from, for example, deuterio, —OH, —NH$_2$, C$_{1-3}$ alkyl, and C$_{1-3}$ alkoxy.

"Therapeutically effective amount" refers to the amount of a compound that, when administered to a subject for treating a disease, or at least one of the clinical symptoms of a disease, is sufficient to affect such treatment of the disease or symptom thereof. A "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation. With reference to a bacterial infection, a therapeutically effective amount can refer to the a therapeutically effective concentration of a compound such as a crystalline anhydrate (1) and/or a β-lactam antibiotic and the site of a bacterial infection. A site of a bacterial infection can refer to an organ or portion of an organ.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or at least one or more symptoms thereof in a patient who may be exposed to or predisposed to a disease or disorder even though that patient does not yet experience or display symptoms of the disease.

Reference is now made to certain compounds and methods. The disclosed embodiments are not intended to be limiting of the claims. To the contrary, the claims are intended to cover all alternatives, modifications, and equivalents.

Avibactam is a β-lactamase inhibitor approved for intravenous use in combination with ceftazidime, a cephalosporin antibiotic, to treat intraabdominal infections, urinary tract infections and pneumonia. Avibactam derivatives that provide therapeutically effective plasma concentrations of avibactam when administered orally have been developed. When co-administered with amoxicillin, the avibactam derivatives provide the opportunity to treat bacterial infections caused by bacteria producing β-lactamase enzymes with oral administration. The avibactam derivatives are sulfonate ester prodrugs of the non-β-lactam β-lactamase inhibitor, avibactam ([2S,5R]-2-carbamoyl-7-oxo-1,6-diazabicyclo[3.2.1]octan-6-yl hydrogen sulfate; (1R,2R,5R)-2-carbamoyl-7-oxo-1,6-diazabicyclo[3.2.1]octan-6-yl hydrogen sulfate (ChemDraw Professional 17.1.0.105 (19)), which has the structure:

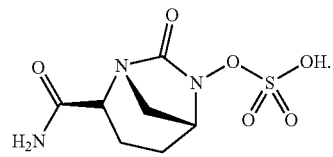

Avibactam derivatives that provide a bioavailability of avibactam in the systemic circulation of a patient and a therapeutically effective concentration of avibactam at the site of an infection following oral administration are disclosed in U.S. Pat. No. 10,085,999. One of the avibactam derivatives that provide an oral bioavailability of avibactam is ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate (1):

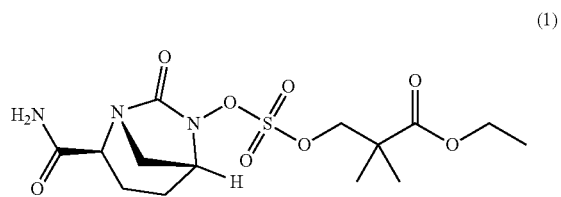

(1)

The synthesis of ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate is described in PCT International Application No. WO 2018/208557.

Sulfate monoester analogs of sulfate-containing compounds can be prepared by reacting a hydroxyl-substituted sulfate-containing compound with a chlorosulfate monoester to provide the corresponding sulfate monoester analog. The methods can be useful in preparing prodrugs of sulfate-containing pharmaceutical compounds.

Prodrugs are derivatized forms of drugs that following administration are converted or metabolized to an active form of the parent drug in vivo. Prodrugs are used to modify one or more aspects of the pharmacokinetics of a drug in a manner that enhances the therapeutic efficacy of a parent drug. For example, prodrugs are often used to enhance the oral bioavailability of a drug. To be therapeutically effective, drugs exhibiting poor oral bioavailability may require frequent dosing, large administered doses, or may need to be administered by other than oral routes, such as intravenously. In particular, many drugs with sulfate groups exhibit poor oral bioavailability.

Intramolecular cyclization prodrug strategies have been used to modify the pharmacokinetics of drugs. Intramolecular cyclization release prodrug strategies have been applied to drugs containing sulfonic acid functional groups. For example, prodrugs comprising a substituted neopentyl sulfonate ester derivative in which the neopentyl group is removed in vivo by unmasking a nucleophilic heteroatom bonded to a substituted neopentyl moiety followed by intramolecular cyclization to generate the parent drug in the sulfonic acid or sulfonic salt form have been described. In such prodrugs the nucleophilic heteroatom can be nitrogen or oxygen and the nitrogen or oxygen nucleophile can be masked with an amine or alcohol protecting group, respectively, capable of being deprotected in vivo.

Sulfate monoester analogs of a sulfate-containing compound can be prepared by reacting a hydroxyl-substituted analog of the sulfate-containing compound with a chlorosulfate monoester under basic conditions, to provide the corresponding sulfate monoester analog. A chlorosulfate monoester can be prepared by reacting sulfuryl chloride with an alcohol having a desired promoiety. For example, sulfate monoester analogs of avibactam provided by the present disclosure can be synthesized by reacting (1R,2S,5R)-6-hydroxy-7-oxo-1,6-diazabicyclo[3.2.1]octane-2-carboxamide with a chlorosulfate monoester having a desired promoiety to provide the corresponding (1R,2S,5R)-2-carbamoyl-7-oxo-1,6-diazabicyclo[3.2.1]octan-6-yl sulfate monoester.

(1R,2S,5R)-6-Hydroxy-7-oxo-1,6-diazabicyclo[3.2.1]octane-2-carboxamide can be prepared by hydrogenating (1R,2S,5R)-6-(benzyloxy)-7-oxo-1,6-diazabicyclo[3.2.1]octane-2-carboxamide using the methods described, for example, in U.S. Pat. Nos. 8,772,490; 9,035,062; and 9,284,273.

(1R,2S,5R)-6-Hydroxy-7-oxo-1,6-diazabicyclo[3.2.1]octane-2-carboxamide can be reacted with the chlorosulfate monoester in the presence of a base to provide the corresponding sulfate monoester analog of avibactam. Suitable methods are disclosed, for example, in *J. Am. Chem. Soc.* 2006, 128, 1605-1610.

Ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate (1):

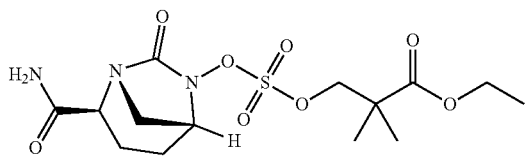

(1)

is a sulfonate ester prodrug of the non-β-lactam β-lactamase inhibitor avibactam ((1R,2S,5R)-2-carbamoyl-7-oxo-1,6-diazabicyclo[3.2.1]octan-6-yl hydrogen sulfate), which has the structure of Formula (2):

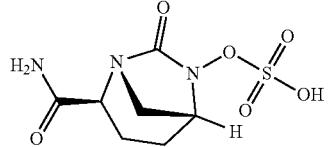

(2)

In the avibactam prodrug of Formula (1), a nucleophilic moiety is positioned proximate to the hydrogen sulfate group. In vivo, the nucleophilic moiety reacts to release the non-β-lactam β-lactamase inhibitor, avibactam. Avibactam is an inhibitor of class A, class C, and certain Class D β-lactamases and is useful in the treatment of bacterial infections when administered in conjunction with β-lactam antibiotics.

Crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1) can be prepared by dissolving ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate in a mixture of ethyl acetate, water, and n-heptane to form a triphasic mixture. The triphasic mixture can comprise, for example, 6 vol % ethyl acetate, 10 vol % water, 3 vol % n-heptane, and 1 vol % ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate.

The triphasic mixture for crystallizing ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate can comprise, for example, 6.5 volumes of ethyl acetate, 10.5 volumes of water, and 13 volumes of n-heptane for each, one volume of ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate. For example, a triphasic mixture can comprise from 4 to 9 volumes of ethyl acetate, from 8 to 13 volumes of water, and from 10 to 16 volumes of n-heptane for each one volume of ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate. For example, a triphasic mixture can comprise from 5 to 8 volumes of ethyl acetate, from 9 to 11 volumes of water, and from 11 to 15 volumes of n-heptane for each one volume of ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate.

After dissolving the ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate (1), the triphasic mixture can be heated to a temperature from 35° C.±5° C. and stirred for at least one hour. The slurry can then be cooled to 5° C.±5° C. over a period of at least 3 hours, and then stirred at 5° C.±5° C. for at least 1 h. The solids are filtered, washed with n-heptane, EtOAc, and water, and dried to provide crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1).

Crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1) is stable following exposure to ambient conditions (25° C./60% RH) and during formulation processing conditions.

Crystalline anhydrate (1) can be characterized by an X-ray powder diffraction (XRPD) pattern having characteristic scattering angles (2θ) at least at 3.16°±0.2°, 6.37°±0.2°, 5.38°±0.2°, and 17.35°±0.2° using the Kα2/Kα1 (0.5) wavelength.

Crystalline anhydrate (1) can be characterized by an XRPD pattern having characteristic scattering angles (2θ) at least at 3.16°±0.1°, 6.37°±0.10, 5.38°±0.10, and 17.35°±0.1° using the Kα2/Kα1 (0.5) wavelength.

Crystalline anhydrate (1) can be characterized by an XRPD pattern having characteristic scattering angles (2θ) at least at 3.16°±0.2°, 6.37±0.2°, 5.38°±0.2°, 15.77°±0.2°, and 17.35°±0.2° using the Kα2/Kα1 (0.5) wavelength.

Crystalline anhydrate (1) can be characterized by an XRPD pattern having characteristic scattering angles (2θ) at least at 3.16°±0.1°, 6.37°±0.10, 5.38°±0.1°, 15.77°±0.10, and 17.35°±0.1° using the Kα2/Kα1 (0.5) wavelength.

Crystalline anhydrate (1) can be characterized by an XRPD pattern having characteristic scattering angles (2θ) at least at 3.16°±0.2°, 6.37°±0.2°, 5.38°±0.2°, 12.75°±0.2°, 15.77°±0.2°, 17.35°±0.2°, 25.68°±0.2°, and 27.13°±0.2° using the Kα2/Kα1 (0.5) wavelength.

Crystalline anhydrate (1) can be characterized by an XRPD pattern having characteristic scattering angles (2θ) at least at 3.16±0.10, 6.37±0.10, 5.38±0.10, 12.75°±0.10, 15.77°±0.10, 17.35°±0.1°, 25.68°±0.10, and 27.13°±0.10 using the Kα2/Kα1 (0.5) wavelength.

Figure 3:
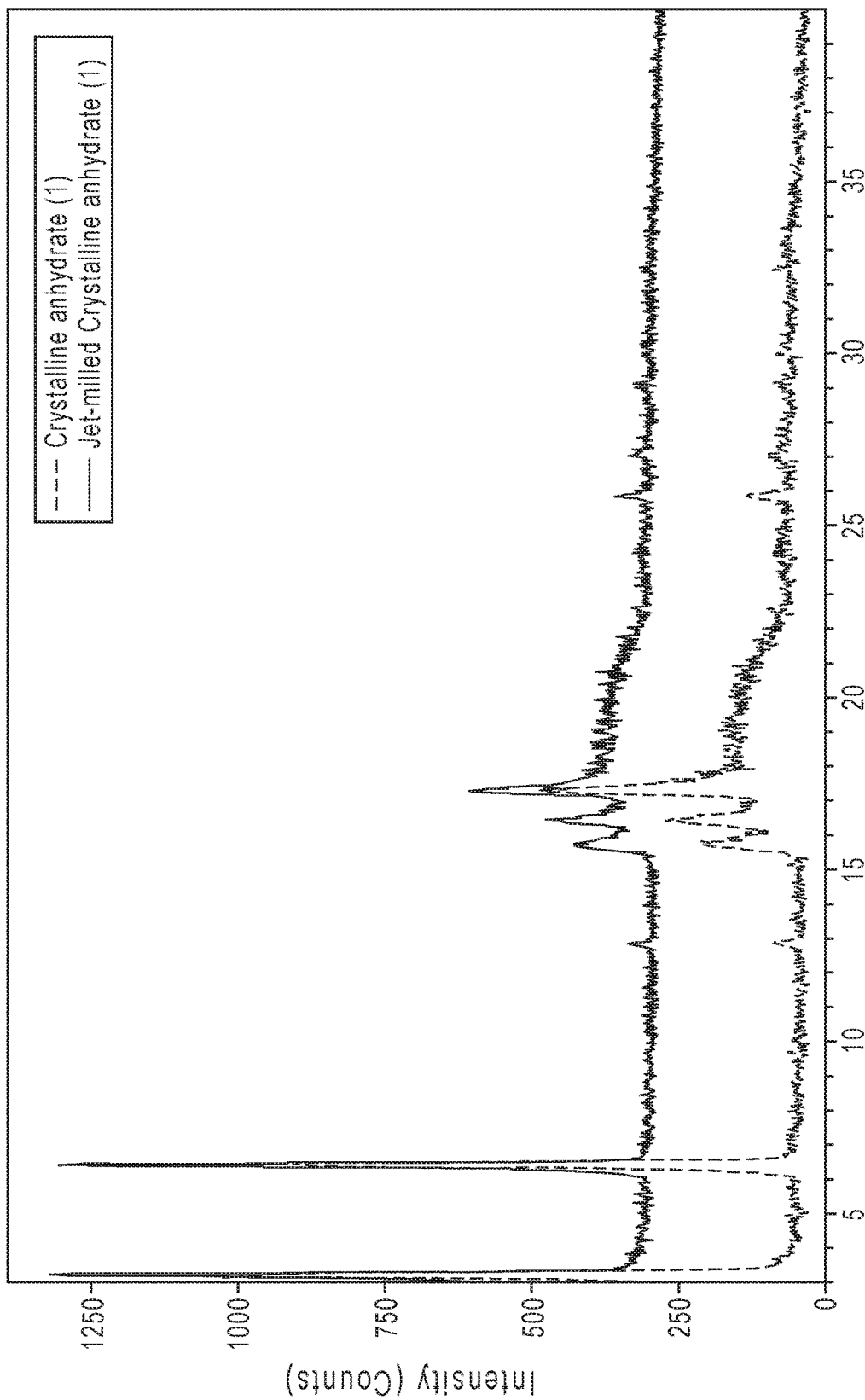
FIG. 3 shows XRPD patterns of crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1) before and after jet-milling.
Figure 6:
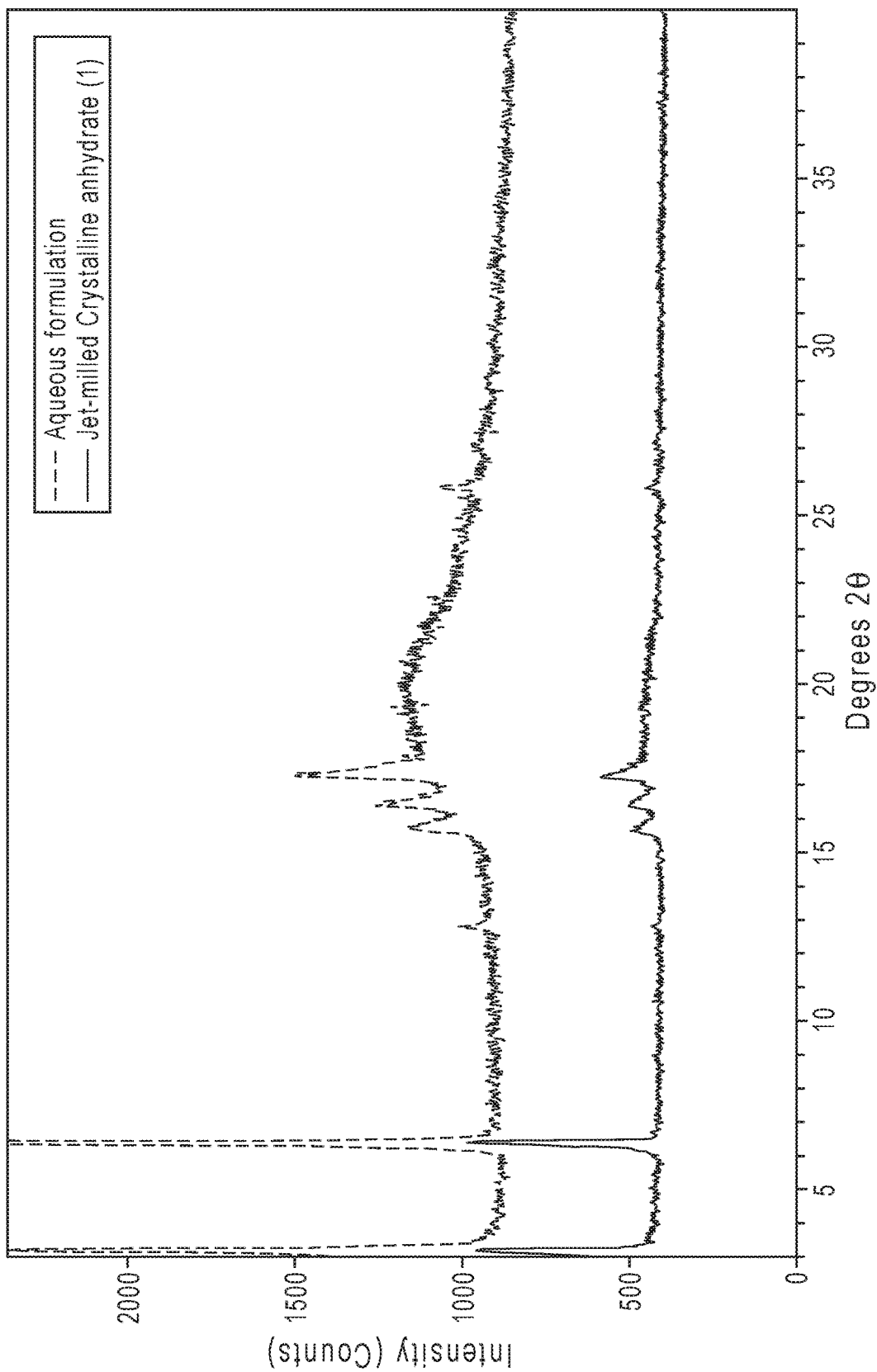
FIG. 6 shows XRPD patterns of crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1) after jet-milling and after suspension in an aqueous formulation at 25° C.

XRPD diffraction patterns of crystalline anhydrate (1) are shown in FIGS. 1, 3 and 6. Crystalline anhydrate (1) can exhibit an XRPD spectrum as substantially shown in FIG. 1, FIG. 3, and/or FIG. 6.

One skilled in the art will recognize that slight variations in the observed ° 2θ diffraction angles can be expected based on, for example, the specific diffractometer employed, the analyst, and the sample preparation technique. Greater variation can be expected for the relative peak intensities. Comparison of diffraction patterns can be based primarily on ° 2θ diffraction angles with a lesser importance attributed to relative peak intensities.

Figure 2:
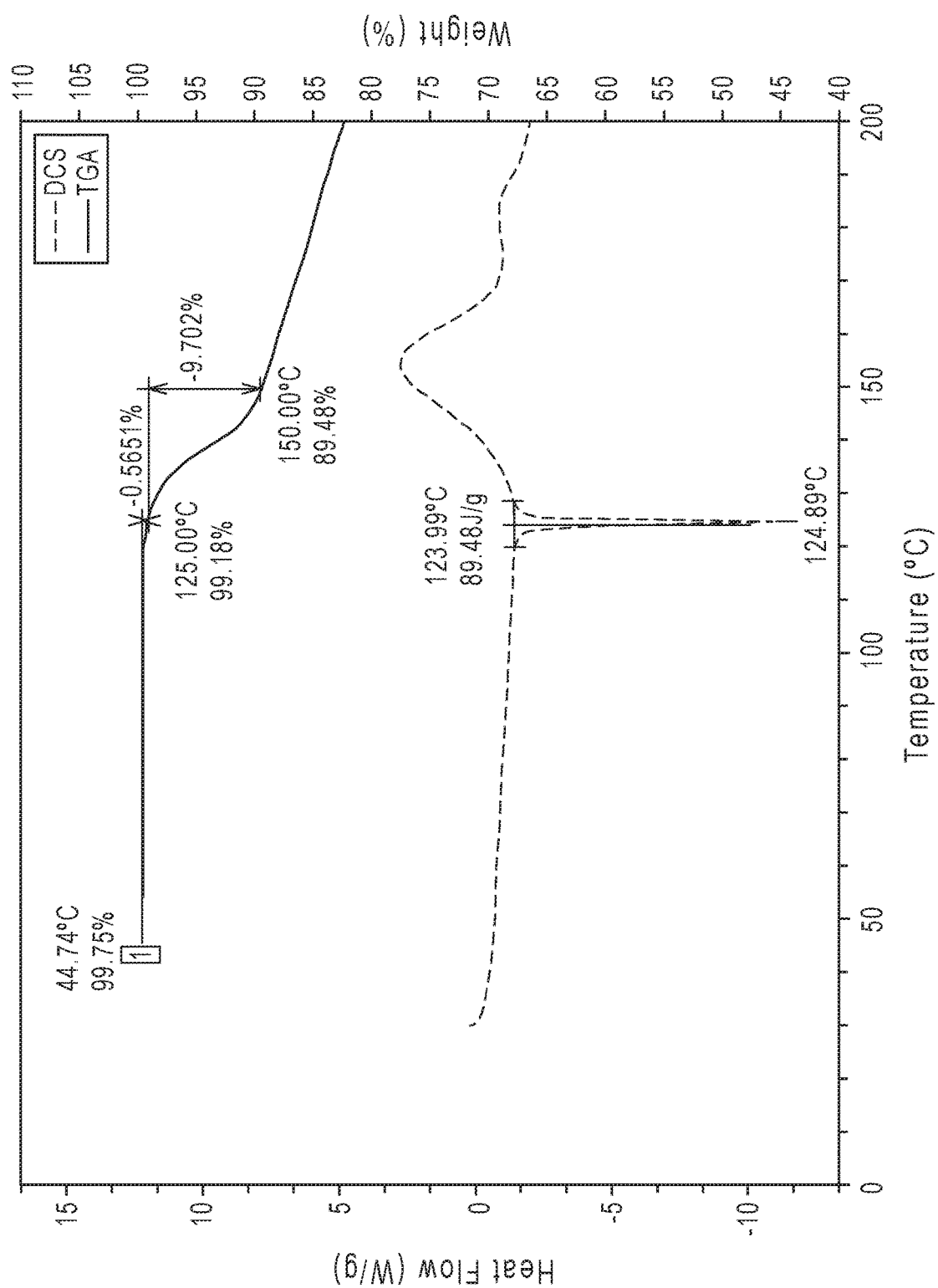
FIG. 2 shows thermogravimetric analysis (TGA) and differential scanning calorimetry (DSC) scans of crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1).
Figure 4:
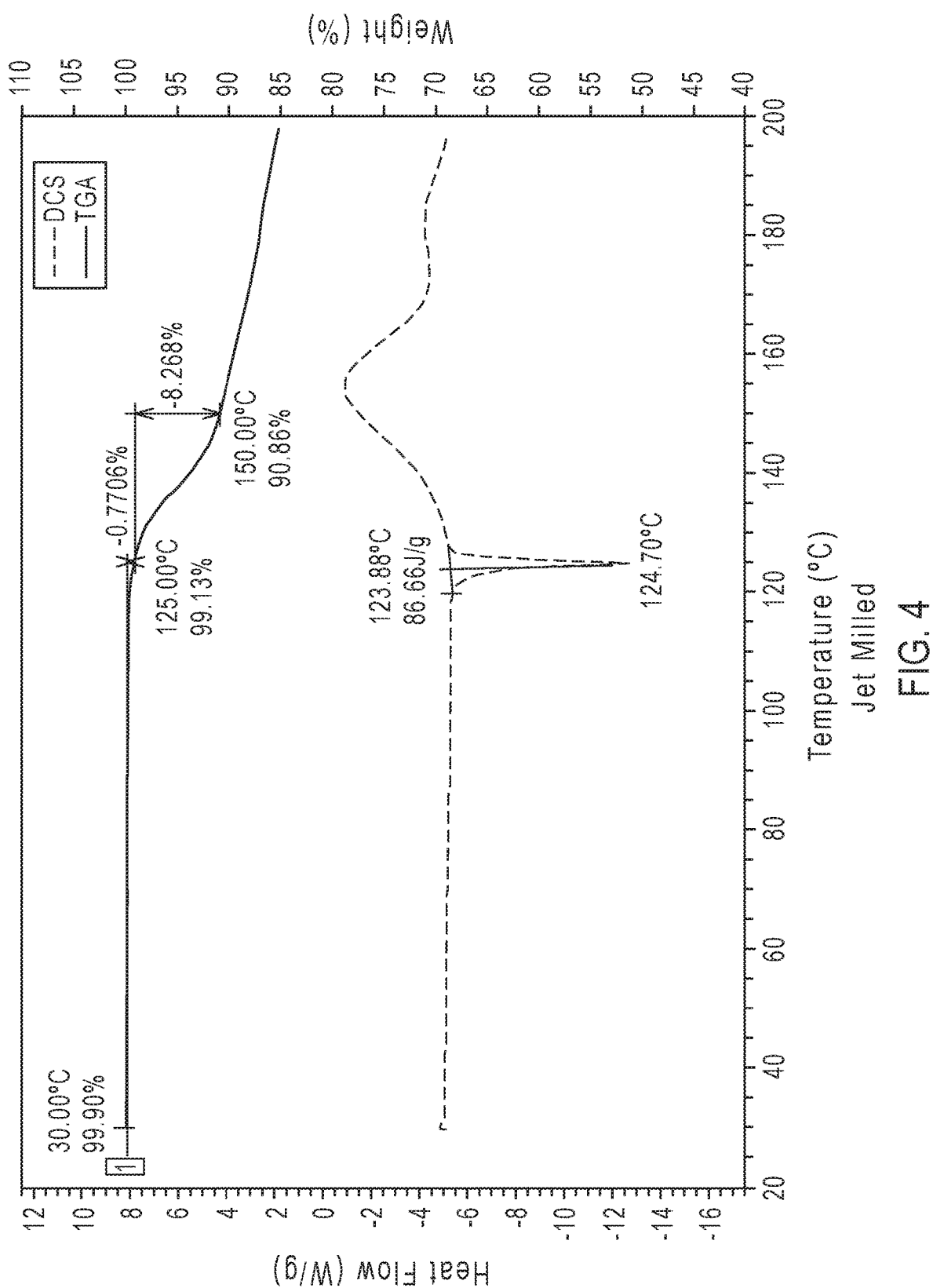
FIG. 4 shows TGA and DSC scans of crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1) after jet milling.

Crystalline anhydrate (1) can be characterized by a melting point, for example, from 123.0° C. to 127.0° C., from 123.0° C. to 126.0° C., from 123.0° C. to 125° C., from 123.5° C. to 124.5° C., 123.8° C. to 124.2° C., or from 123.9° C. to 124.1° C., such as 123.99° C. as determined using differential scanning calorimetry (DSC). DSC scans of crystalline anhydrate (1) are shown in FIGS. 2 and 4. Crystalline anhydrate (1) can exhibit a DSC scan as substantially shown in FIG. 2 and/or FIG. 4.

Crystalline anhydrate (1) can have a weight loss from 7.2% to 9.2%, such as from 7.6% to 8.8%, from 8% to 8.4%, or from 8.1% to 8.3% over a temperature range from 125° C. to 150° C. as determined by thermogravimetric analysis (TGA). There is no appreciable weight loss over the range from 30° C. to 125° C. Crystalline anhydrate (1) can exhibit a TGA scan as substantially shown in FIG. 2 and/or FIG. 4.

Figure 5:
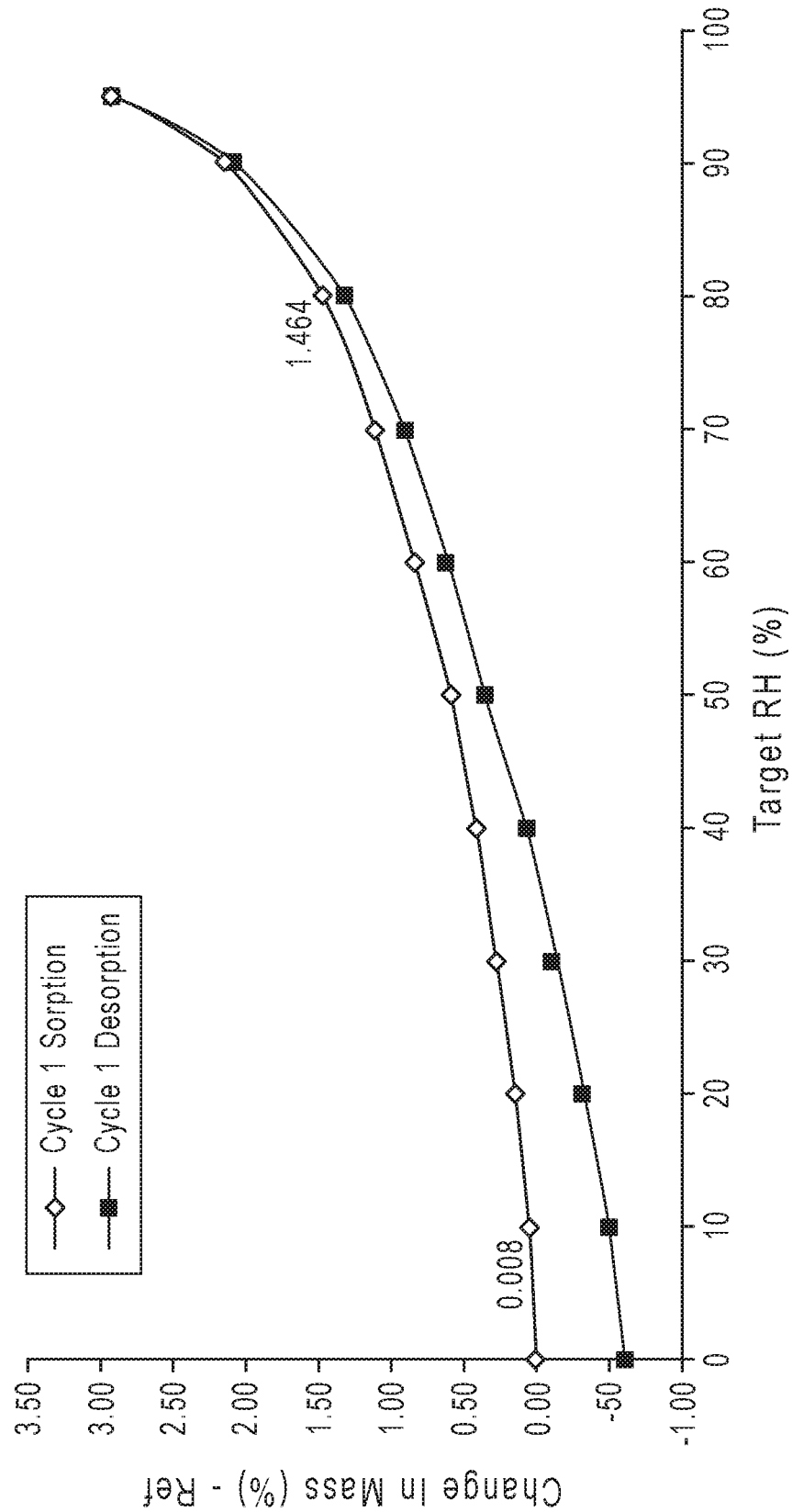
FIG. 5 shows a Dynamic Vapor Sorption (DVS) isotherm of crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1).

Crystalline anhydrate (1) can exhibit a reversible moisture absorption over a range of humidity from 0% RH to 95% RH with a maximum increase in mass of about 3 wt % at 25° C./95% RH. A dynamic vapor sorption (DVS) scan is shown in FIG. 5. Crystallin anhydrate (1) can exhibit a DVS scan as substantially shown in FIG. 5. Crystalline anhydrate (1) as a powder can be stable during storage at 25° C./60% RH for a duration, for example, of 4 weeks, for 8 weeks, or for 12 weeks. By storage stable is meant that the properties of the crystalline anhydrate (1) in powder form such as the XRPD spectrum, the melting point, the weight loss, and the moisture absorption are substantially the same before and after storage at 25° C./60% RH for the indicated period of time. By substantially the same is meant that the values differ, for example, by less than 5%, by less than 2%, or by less than 1%.

Crystalline anhydrate (1) was jet milled to obtain a uniform particle size of less than 10 μm for use in pharmaceutic formulations. XRPD patterns of crystalline anhydrate (1) before and after jet-milling are compared in FIG. 3 and show that the crystalline form before and after jet-milling is the same. TGA and DSC scans of the jet-milled material are shown in FIG. 4 and are similar to those for the un-milled material shown in FIG. 2.

Pharmaceutical compositions provided by the present disclosure can comprise crystalline anhydrate (1) and a pharmaceutically acceptable excipient.

An aqueous formulation of crystalline anhydrate (1) was prepared by suspending 100 mg crystalline anhydrate (1) in 100 mL of an aqueous solution containing 0.25 wt % Tween® 80, 10 wt % PEG 400, 0.5 wt % methylcellulose (400 cps), and a pH 3.0 citrate buffer, where wt % is based on the total weight of the aqueous formulation. The suspension was sonicated and left for 24 hours at 25° C. before filtering out the crystalline anhydrate (1).

XRPD patterns of the jet-milled crystalline anhydrate (1) and the material obtained from the filtered suspension are compared in FIG. 6.

Crystalline anhydrate (1) may be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. Pharmaceutical compositions provided by the present disclosure can be provided as oral formulations. Oral formulations may be oral dosage forms.

Pharmaceutical compositions provided by the present disclosure may comprise a therapeutically-effective amount of crystalline anhydrate (1). Pharmaceutical compositions provided by the present disclosure may comprise a therapeutically-effective amount of crystalline anhydrate (1) together with a suitable amount of one or more pharmaceutically acceptable vehicles so as to provide a composition for administration to a patient. Suitable pharmaceutically acceptable vehicles and methods of preparing pharmaceutical compositions are described in the art. Examples of suitable pharmaceutically acceptable vehicles are also described in the art.

Pharmaceutical compositions comprising crystalline anhydrate (1) may be manufactured by means of conventional mixing, dissolving, granulating, milling, levitating, emulsifying, encapsulating, entrapping or lyophilizing processes. Pharmaceutical compositions may be formulated in a suitable manner using one or more pharmaceutically acceptable vehicles which facilitate processing of compounds into preparations which can be used pharmaceutically. Suitable formulation is dependent upon the route of administration chosen.

Crystalline anhydrate (1) may be incorporated into pharmaceutical compositions to be administered orally. Oral administration of such pharmaceutical compositions may result in uptake of crystalline anhydrate (1) throughout or in a portion of the gastrointestinal tract and entry into the systemic circulation. Such compositions may be prepared in a manner known in the pharmaceutical art and can comprise crystalline anhydrate (1) and at least one pharmaceutically acceptable vehicle.

In preparing a pharmaceutical composition, it may be useful to mill crystalline anhydrate (1) to provide an appropriate particle size prior to combining with other ingredients. The milled particle size of crystalline anhydrate (1) may be adjusted depending on the aqueous solubility, and can be, for example, less than 50 μm, less than 40 μm, less than 30 μm, less than 10 μm, or less than 5 μm. The compositions may be formulated so as to provide immediate, controlled, sustained, or delayed release of crystalline anhydrate (1) after oral administration to the patient by employing procedures known in the art.

A composition may be formulated in unit dosage form, each dosage form comprising an equivalent weight of crystalline anhydrate (1) within a range, for example, from 10 mg to 10 g. A unit dosage form refers to a physically discrete unit suitable as a unitary dosage for humans and other mammals, each unit containing a predetermined quantity of active material calculated to produce an intended therapeutic effect, in association with a suitable pharmaceutical excipient, diluent, carrier and/or adjuvant.

For preparing solid compositions such as tablets, crystalline anhydrate (1) may be mixed with a pharmaceutically acceptable vehicle including, for example, excipients, diluents, carriers and/or adjuvants to form a solid pre-formulation composition containing a homogeneous mixture containing crystalline anhydrate (1). When referring to these pre-formulation compositions as homogeneous, it is meant that crystalline anhydrate (1) is dispersed evenly throughout the composition so that the composition can be readily subdivided into equally effective unit dosage forms such as tablets, pills, or capsules.

An oral formulation comprising crystalline anhydrate (1) can be adapted to provide controlled and/or sustained release of crystalline anhydrate (1) following oral administration.

Regardless of the oral dosage form used, crystalline anhydrate (1) may be released from an orally administered dosage form, over a sufficient period of time to provide therapeutic concentrations of avibactam in the blood of a patient. Following oral administration, dosage forms comprising crystalline anhydrate (1) can provide a therapeutic or prophylactic concentration of avibactam in the plasma and/or blood of a patient for a time period, for example, of at least about 4 hours, for at least about 8 hours, for at least about 12 hours, for at least about 16 hours, for at least about 20 hours, or for at least about 24 hours following oral administration of an oral dosage form comprising crystalline anhydrate (1). A therapeutically or prophylactically effective concentration of avibactam in the blood and/or plasma of a patient can depend on a number of factors including, for example, the disease being treated, the severity of the disease, the weight of the patient, the health of the patient, and so forth.

The appropriate oral dosage form for a particular pharmaceutical composition provided by the present disclosure may depend, at least in part, on the gastrointestinal absorption properties of crystalline anhydrate (1), the stability of crystalline anhydrate (1) in the gastrointestinal tract, the pharmacokinetics of crystalline anhydrate (1) and/or avibactam, and the therapeutic profile. An appropriate controlled release oral dosage form may be selected for a particular compound of crystalline anhydrate (1). For example, gastric retention oral dosage forms may be appropriate for compounds absorbed primarily from the upper gastrointestinal tract, and sustained release oral dosage forms may be appropriate for compounds absorbed primarily from the lower gastrointestinal tract.

Pharmaceutical compositions provided by the present disclosure may be provided as dosage forms adapted to provide sustained release of crystalline anhydrate (1) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

Crystalline anhydrate (1) and pharmaceutical compositions provided by the present disclosure may be administered for therapeutic or prophylactic treatments. A therapeutic amount is an amount sufficient to remedy a disease state or symptoms, or otherwise prevent, hinder, retard, or reverse the progression of disease or any other undesirable symptoms in any way whatsoever. In prophylactic applications, pharmaceutical compositions of the present disclosure may be administered to a patient susceptible to or otherwise at risk of a particular disease or infection. Hence, a prophylactically effective amount is an amount sufficient to prevent, hinder or retard a disease state or its symptoms.

An appropriate dosage of the pharmaceutical composition may be determined according to any one of several well-established protocols. For example, animal studies, such as studies using mice or rats, may be used to determine an appropriate dose of a pharmaceutical compound. Results based on animal studies can be extrapolated to determine doses for use in other species, such as for example, humans. For example, the efficacy of crystalline anhydrate (1) and compositions thereof for treating an infectious disease may be assessed using animal and human models of infectious disease and clinical studies. Crystalline anhydrate (1) and pharmaceutical compositions thereof may be administered as sustained release systems, and in certain embodiments, as orally administered sustained release systems. Crystalline anhydrate (1) may be delivered by oral sustained release administration. Crystalline anhydrate (1) and pharmaceutical compositions thereof may be orally administered, for example, three times per day, two per day, once per day, or at intervals greater than once per day.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of crystalline anhydrate (1) and appropriate dosing intervals may be selected to maintain a sustained therapeutically effective concentration of avibactam in the blood of a patient, and in certain embodiments, without exceeding a minimum adverse concentration.

An administered dose can be less than a toxic dose. Toxicity of doses of crystalline anhydrate (1) can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Crystalline anhydrate (1) may exhibit a high therapeutic index. A dose of crystalline anhydrate (1) may be within a range of circulating concentrations in for example the blood, plasma, or central nervous system, that include the effective dose and that exhibits little or no toxicity. A dose may vary within this range depending upon the dosage form employed and the route of administration utilized.

Pharmaceutical compositions comprising crystalline anhydrate (1) may be administered once per day, twice per day, and in certain embodiments at intervals of more than once per day. Dosing may be provided alone or in combination with other drugs and may continue as long as required for effective treatment of a disease such as a bacterial infection. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of crystalline anhydrate (1) contained within each of the multiple dosage forms may be the same or different.

Suitable daily dosage ranges for administration may range from about 2 µg to about 20 mg of crystalline anhydrate (1) per kilogram body weight.

Suitable daily dosage ranges for administration may range from about 1 µg to about 50 mg of crystalline anhydrate (1) per square meter ($m^2$) of body surface.

Crystalline anhydrate (1) may be administered to treat an infectious disease in a patient in an amount, for example, from about 1 mg to about 2,000 mg per day, from about 100 µg to about 1,500 mg per day, from about 20 µg to about 1,000 mg per day, or in any other appropriate daily dose.

Pharmaceutical compositions comprising crystalline anhydrate (1) may be administered to treat an infectious disease in a patient and provide a therapeutically effective concentration of avibactam in the blood or plasma of the patient. A therapeutically effective concentration of avibactam in the blood or plasma of a patient can be, for example, from about 1 µg/mL to about 60 µg/mL, from about 2 µg/mL to about 50 µg/mL, from about 5 µg/mL to about 40 µg/mL, from about 5 µg/mL to about 20 µg/mL, or from about 5 µg/mL to about 10 µg/mL. A therapeutically effective concentration of avibactam in the blood or plasma of a patient can be, for example, at least about 2 µg/mL, at least about 5 µg/mL, at least about 10 µg/mL, at least about 15 µg/mL, at least about 25 µg/mL, or at least about 30 µg/mL. A therapeutically effective concentration of avibactam in the blood or plasma of a patient can be less than an amount that causes unacceptable adverse effects including adverse effects to homeostasis. A therapeutically effective concentration of avibactam in the blood or plasma of a patient can be an amount sufficient to restore and/or maintain homeostasis in the patient. For example, following administration of a therapeutically effective dose of crystalline anhydrate (1), a therapeutically effective amount of avibactam can be maintained in the blood of the patient for greater than 1 hour, greater than 2 hours, greater than 3 hours, greater than 4 hours, greater than 5 hours, greater than 6 hours, greater than 7 hours, or greater than 8 hours. For example, following administration of a therapeutically effective dose of crystalline anhydrate (1), a therapeutically effective amount of avibactam can be maintained, for example, from 1 hour to 10 hours, from 2 hours to 8 hours, from 2 hours to 6 hours, or from 2 hours to 4 hours.

Pharmaceutical compositions comprising crystalline anhydrate (1) may be administered to treat an infectious disease in a patient so as to provide a therapeutically effective concentration of avibactam in the blood or plasma of a patient for an extended period of time such as, for example, for at least about 4 hours, for at least about 6 hours, for at least about 8 hours, for at least about 10 hours, and in certain embodiments, for at least about 12 hours.

The amount of crystalline anhydrate (1) administered may vary during a treatment regimen.

Pharmaceutical compositions provided by the present disclosure may further comprise one or more pharmaceutically active compounds in addition to crystalline anhydrate (1). Such compounds may be provided to treat the infectious disease being treated with crystalline anhydrate (1) or to treat a disease, disorder, or condition other than the infectious disease being treated with crystalline anhydrate (1).

Crystalline anhydrate (1) may be used in combination with at least one other therapeutic agent. Crystalline anhydrate (1) may be administered to a patient together with another therapeutic agent for treating an infectious disease in the patient. Crystalline anhydrate (1) and the at least one other therapeutic agent may act additively or, and in certain embodiments, synergistically. The at least one additional therapeutic agent may be included in the same pharmaceutical composition or vehicle comprising crystalline anhydrate (1) or may be in a separate pharmaceutical composition or vehicle. Accordingly, methods provided by the present disclosure further include, in addition to administering crystalline anhydrate (1), administering one or more therapeutic agents effective for treating an infectious disease or a different disease, disorder or condition than the infectious disease. Methods provided by the present disclosure include administration of crystalline anhydrate (1) and one or more other therapeutic agents provided that the combined administration does not inhibit the therapeutic efficacy of crystalline anhydrate (1) and/or does not produce adverse combination effects.

Pharmaceutical compositions comprising crystalline anhydrate (1) may be administered concurrently with the administration of another therapeutic agent, which may be part of the same pharmaceutical composition as, or in a different pharmaceutical composition than that comprising crystalline anhydrate (1). Crystalline anhydrate (1) may be administered prior to or subsequent to administration of another therapeutic agent. In certain combination therapies, the combination therapy may comprise alternating between administering crystalline anhydrate (1) and a composition comprising another therapeutic agent, e.g., to minimize adverse drug effects associated with a particular drug and/or to enhance treatment efficacy. When crystalline anhydrate (1) is administered concurrently with another therapeutic agent that potentially may produce an adverse drug effect including, for example, toxicity, the other therapeutic agent may be administered at a dose that falls below the threshold at which the adverse drug reaction is elicited.

Pharmaceutical compositions comprising crystalline anhydrate (1) may be administered with one or more substances to enhance, modulate and/or control release, bioavailability, therapeutic efficacy, therapeutic potency, and/or stability crystalline anhydrate (1). For example, to enhance the therapeutic efficacy of crystalline anhydrate (1), crystalline anhydrate (1) may be co-administered with one or more active agents to increase the absorption or diffusion of crystalline anhydrate (1) from the gastrointestinal tract to the systemic circulation, or to inhibit degradation of crystalline anhydrate (1) in the blood of a patient. A pharmaceutical composition comprising crystalline anhydrate (1) may be co-administered with an active agent having pharmacological effects that enhance the therapeutic efficacy of crystalline anhydrate (1).

Crystalline anhydrate (1) or a pharmaceutical composition comprising crystalline anhydrate (1) may be administered in conjunction with an agent known or believed to be effective in treating an infectious disease in a patient.

Crystalline anhydrate (1) or a pharmaceutical composition of crystalline anhydrate (1) may be included in a kit that may be used to administer the compound to a patient for therapeutic purposes. A kit may include a pharmaceutical composition comprising crystalline anhydrate (1) suitable for administration to a patient and instructions for administering the pharmaceutical composition to the patient. A kit for use in treating a bacterial infection in a patient can comprise crystalline anhydrate (1), a pharmaceutically acceptable vehicle for administering the compound, and instructions for administering the compound to a patient. A kit can further comprise a β-lactam antibiotic or a combination of β-lactam antibiotics. Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Crystalline anhydrate (1) and compositions provided by the present disclosure can be administered orally. Crystalline anhydrate (1), when orally administered, provide an enhanced oral bioavailability of avibactam compared to the oral bioavailability of orally administered avibactam. For example, crystalline anhydrate (1) can exhibit an oral bioavailability (% F) of at least 10%, at least 20%, at least 30%, at least 40%, at least 50%, or at least 60%. Crystalline anhydrate (1) can provide an oral availability of avibactam, for example, from 5% to 90% from, 10% to 80%, from 15% to 70%, or from 20% to 60%. The oral bioavailability of avibactam is less than 1%.

Crystalline anhydrate (1) is a prodrug of the β-lactamase inhibitor avibactam. Crystalline anhydrate (1) can be used to treat a disease in which the etiology of the disease is associated with the expression of β-lactamases. For example, certain bacterial infections are resistant to β-lactamase antibiotics because β-lactamases produced by the bacteria hydrolyze the β-lactam ring of the β-lactam antibiotic. Crystalline anhydrate (1) can be used in combination with a β-lactam antibiotic to treat a bacterial infection in a patient where the combination of avibactam and the β-lactam antibiotic is effective in treating the bacterial infection.

Crystalline anhydrate (1) can be used to treat a bacterial disease in a patient.

Crystalline anhydrate (1) and pharmaceutical compositions provided by the present disclosure can be used to treat a bacterial disease in which avibactam is effective in treating the bacterial disease such as a bacterial infection where the bacteria causing the infection generate β-lactamases.

Crystalline anhydrate (1) can be used to treat a bacterial infection or a disease caused by a bacterial infection in a patient such as an infection or disease caused by gram-negative bacteria and/or gram-positive bacteria. For example, compounds and pharmaceutical compositions provided by the present disclosure can be used to treat a bacterial infection associated with bacteria such as obligate aerobic bacteria, obligate anaerobic bacteria, faculative anaerobic bacteria, and microaerophilic bacteria.

Examples of obligate aerobic bacteria include gram-negative cocci such as *Moraxella catarrhalis*, *Neisseria gonorrhoeae*, and *N. meningitidi*; gram-positive bacilli such as *Corynebacterium jeikeium*; acid-fast bacilli such as *Mycobacterium avium* complex, *M. kansasii*, *M. leprae*, *M. tuberculosis*, and *Nocardia* sp; nonfermentative, non-enterobacteriaceae such as *Acinetobacter calcoaceticus*, *Elizabethkingia meningoseptica* (previously *Flavobacterium meningosepticum*), *Pseudomonas aeruginosa*, *P. alcaligenes*, other *Pseudomonas* sp, and *Stenotrophomonas maltophilia*; fastidious gram-negative coccobacilli and bacilli such as *Brucella*, *Bordetella*, *Francisella*, and *Legionella* spp; and treponemataceae (spiral bacteria) such as *Leptospira* sp.

Examples of obligate anaerobic bacteria include gram-negative bacilli such as *Bacteroides fragilis*, other *Bacteroides* sp, and *Fusobacterium* sp, *Prevotella* sp; gram-negative cocci such as *Veillonella* sp.; gram-positive cocci such as *Peptococcus niger*, and *Peptostreptococcus* sp.; non-spore-forming gram-positive bacilli such as *Clostridium botulinum*, *C. perfringens*, *C. tetani*, other *Clostridium* sp; and endospore-forming gram-positive bacilli such as *Clostridium botulinum*, *C. perfringens*, *C. tetani*, and other *Clostridium* sp.

Examples of facultative anaerobic bacteria include gram-positive cocci, catalase-positive such as *Staphylococcus aureus* (coagulase-positive), *S. epidermidis* (coagulase-negative), and other coagulase-negative staphylococci; gram-positive cocci, catalase-negative such as *Enterococcus faecalis*, *E. faecium*, *Streptococcus agalactiae* (group B streptococcus), *S. bovis*, *S. pneumoniae*, *S. pyogenes* (group A streptococcus), viridans group streptococci (*S. mutans*, *S. mitis*, *S. salivarius*, *S. sanguis*), *S. anginosus* group (*S. anginosus*, *S. milleri*, *S. constellatus*), and *Gemella morbillorum*; gram-positive bacilli such as *Bacillus anthracis*, *Erysipelothrix rhusiopathiae*, and *Gardnerella vaginalis* (gram-variable); gram-negative bacilli such as Enterobacteriaceae (*Citrobacter* sp, *Enterobacter aerogenes*, *Escherichia coli*, *Klebsiella* sp, *Morganella morganii*, *Proteus* sp, *Plesiomonas shigelloides*, *Providencia rettgeri*, *Salmonella typhi*, other *Salmonella* sp, *Serratia marcescens*, and *Shigella* sp, *Yersinia enterocolitica*, *Y. pestis*); fermentative, non-Enterobacteriaceae such as *Aeromonas hydrophila*, *Chromobacterium violaceum*, and *Pasteurella multocida*; fastidious gram-negative coccobacilli and bacilli such as *Actinobacillus actinomycetemcomitans*, *Bartonella bacilliformis*, *B. henselae*, *B. quintana*, *Eikenella corrodens*, *Haemophilus influenzae*, and other *Haemophilus* sp; mycoplasma such as *Mycoplasma pneumoniae*; and treponemataceae (spiral bacteria) such as *Borrelia burgdorferi*, and *Treponema pallidum*.

Examples of microaerophilic bacteria include curved bacilli such as *Campylobacter jejuni*, *Helicobacter pylori*, *Vibrio cholerae*, and *V. vulnificus*; obligate intracellular parasitic; chlamydiaceae such as *Chlamydia trachomatis*, *Chlamydophila pneumoniae*, and *C. psittaci*; coxiellaceae such as *Coxiella burnetii*; and rickettsiales such as *Rickettsia prowazekii*, *R. rickettsii*, *R. typhi*, *R. tsutsugamushi*, *Ehrlichia chaffeensis*, and *Anaplasma phagocytophilum*.

An infectious disease can be a bacterial infection caused by a gram-negative bacteria such as, for example, *Acinetobacter*, *Aeromonas*, *Bacteroides*, *Burkholderia*, *Citrobacter*, *Enterobacter*, *Escherichia*, *Fusobacterium*, *Haemophilus*, *Klebsiella*, *Moraxella*, *Morganella*, *Mycoplasma*, *Neisseria*, *Pantoea*, *Pasteurella*, *Plesiomonas*, *Porphyromonas*, *Prevotella*, *Proteus*, *Providencia*, *Pseudomonas*, *Salmonella*, *Serratia*, *Shigella*, *Spirillum*, *Stenotrophomonas*, *Streptobacillus*, *Treponema*, and *Yersinia*. Additional examples of gram-negative bacteria include *Acinetobacter baumannii*, *Aeromonas hydrophila*, *Arizona hinshawii*, *Bacteroides fragilis*, *Branhamella catarrhalis*, *Burkholderia cepacia*, *Citrobacter diversus*, *Citrobacter freundii*, *Enterobacter aerogenes*, *Enterobacter cloacae*, *Escherichia coli*, *Fusobacterium nucleatum*, *Haemophilus influenzae*, *Haemophilus parainfluenzae*, *Klebsiella oxytoca*, *Klebsiella pneumoniae*, *Moraxella catarrhalis*, *Morganella morganii*, *Neisseria gonorrhoeae*, *Neisseria meningitidis*, *Pantoea agglomerans*, *Pasteurella multocida*, *Plesiomonas shigelloides*, *Prevotella melaninogenica*, *Proteus mirabilis*, *Proteus rettgeri*, *Proteus vulgaris*, *Pseudomonas aeruginosa*, *Pseudomonas diminuta*, *Pseudomonas fluorescens*, *Pseudomonas stutzeri*, *Salmonella enterica*, *Salmonella enteritidis*, *Salmonella typhi*, *Serratia marcescens*, *Spirillum minus*, *Stenotrophomonas maltophilia*, *Streptobacillus moniliformis*, *Treponema pallidum*, and *Yersinia enterocolitica*.

Crystalline anhydrate (1) and pharmaceutical compositions thereof can be used to treat an infectious disease caused by *Citrobacter* species, *Enterobacter* species, *Escherichia coli*, *Haemophilus influenzae*, *Klebsiella pneumoniae*, *Proteus mirabilis*, *Pseudomonas aerugiosa*, *Serratia species*,

*Aeromonas hydrophila, Morganella morganii, Neisseria gonorrhoeae, Pasteurella multocida, Proteus vulgaris, Providencia stuartii, Providencia rettgeri,* or *Yersinia enterocolitica.*

The development of antibiotic resistance continues to grow as a problem facing patients and clinicians. Accordingly, the U.S. Food and Drug Administration has identified the following pathogens as presenting a potentially serious threat to public health: *Acinetobacter* species, *Aspergillus* species, *Burkholderia cepacia* complex, *Campylobacter* species, *Candida* species, *Clostridium difficile, Coccidioides species, Cryptococcus* species, Enterobacteriaceae (e.g., *Klebsiella pneumoniae*), *Enterococcus* species, *Helicobacter pylori, Mycobacterium tuberculosis* complex, *Neisseria gonorrhoeae, N. meningitidis,* non-tuberculous mycobacteria species, *Pseudomonas* species, *Staphylococcus aureus, Streptococcus agalactiae, S. pneumoniae, S. pyogenes,* and *Vibrio cholerae.* The FDA has designated these organisms "qualifying pathogens" for purposes of the Generating Antibiotic Incentives Now (GAIN) Act, intended to encourage development of new antibacterial and antifungal drugs for the treatment of serious or life-threatening infections. Other types of bacteria can be added or subtracted from the list of "qualifying pathogens" and the methods provided by the present disclosure encompass any newly added bacteria. Crystalline anhydrate (1), compositions thereof, methods, and kits provided by the present disclosure are useful for the treatment of diseases, infections, etc. caused by many of these organisms.

Crystalline anhydrate (1) and pharmaceutical compositions thereof may be used treat or prevent various diseases caused by the listed bacteria. These include, for example, venereal disease, pneumonia, complicated urinary tract infections, urinary tract infections, complicated intra-abdominal infections and intra-abdominal infections.

Crystalline anhydrate (1) and pharmaceutical compositions thereof can be administered to a patient to inhibit a β-lactamase. Crystalline anhydrate (1) and pharmaceutical compositions thereof can be administered to a patient to inhibit any suitable type of β-lactamase. Examples of suitable β-lactamases include extended-spectrum β-lactamases such as TEM β-lactamases (Class A), SHV β-lactamases (Class A), CTX-M β-lactamases (Class A), OXA β-lactamases (Class D), and other extended spectrum β-lactamases such as PER, VEB, GES, and IBC β-lactamases; inhibitor-resistant β-lactamases; AmpC-type-β lactamases (Class C); carbapenemases such as IMP-type carbapenemases (metallo-β-lactamases) (Class B), VIM (verona integron-encoded metallo-β-lactamase (Class B), OXA (oxcillinase) group β-lactamases (Class D), KPC (*K. pneumoniae* carbapenemase) (Class A), CMY (Class C), SME, IMI, NMC, and CcrA, and NDM-1 (New Delhi metallo-β-lactamase) (Class B).

Examples of suitable β-lactamases also include cephalosporinases, penicillinases, cephalosporinases, broad-spectrum β-lactamases, extended-spectrum β-lactamases, inhibitor-resistant 3-lactamases, carbenicillinase, cloxicillinases, oxacillinases, carbapenemases, and metalloenzymes.

Types of β-lactamases include Class A, Class B, Class C, and Class D β-lactamases.

Crystalline anhydrate (1) and pharmaceutical compositions thereof can be administered orally.

Crystalline anhydrate (1) and pharmaceutical compositions thereof, when orally administered, provide an enhanced oral bioavailability of the β-lactamase inhibitor avibactam compared to the oral bioavailability of avibactam when orally administered, which is less than 5%. For example, crystalline anhydrate (1) can exhibit an oral bioavailability (% F) of at least 10%, at least 20%, at least 30%, at least 40%, at least 50%, or at least 60%. For example, crystalline anhydrate (1) can exhibit an oral bioavailability (% F) of greater than 10%, greater than 20%, greater than 30%, greater than 40%, greater than 50%, greater than 60%, greater than 70%, greater than 80%, or greater than 90%.

Pharmaceutical compositions provided by the present disclosure may further comprise one or more pharmaceutically active compounds in addition to crystalline anhydrate (1). Such compounds may be provided to treat the bacterial infection being treated with crystalline anhydrate (1) or to treat a disease, disorder, or condition other than the bacterial infection being treated with crystalline anhydrate (1).

Crystalline anhydrate (1) may be used in combination with at least one other therapeutic agent. Crystalline anhydrate (1) may be administered to a patient together with another compound for treating a bacterial infection in the patient. Crystalline anhydrate (1) and the at least one other therapeutic agent may act additively or synergistically. The at least one additional therapeutic agent may be included in the same pharmaceutical composition or vehicle comprising crystalline anhydrate (1) or may be in a separate pharmaceutical composition or vehicle. Accordingly, methods provided by the present disclosure further include, in addition to administering crystalline anhydrate (1), administering one or more therapeutic agents effective for treating a bacterial infection or a different disease, disorder or condition than the bacterial infection being treated with crystalline anhydrate (1). Methods provided by the present disclosure include administration of crystalline anhydrate (1) and one or more other therapeutic agents provided that the combined administration does not inhibit the therapeutic efficacy of crystalline anhydrate (1) and/or does not produce adverse combination effects.

Pharmaceutical compositions comprising crystalline anhydrate (1) may be administered concurrently with the administration of another therapeutic agent, which may be part of the same pharmaceutical composition as, or in a different pharmaceutical composition than that comprising crystalline anhydrate (1). Crystalline anhydrate (1) may be administered prior or subsequent to administration of another therapeutic agent. In certain combination therapies, the combination therapy may comprise alternating between administering crystalline anhydrate (1) and another therapeutic agent, e.g., to minimize adverse drug effects associated with a particular drug. When crystalline anhydrate (1) is administered concurrently with another therapeutic agent that potentially may produce an adverse drug effect including, for example, toxicity, the other therapeutic agent may be administered at a dose that falls below the threshold at which the adverse drug reaction is elicited.

Pharmaceutical compositions comprising crystalline anhydrate (1) may be administered with one or more substances to enhance, modulate and/or control release, bioavailability, therapeutic efficacy, therapeutic potency, and/or stability of crystalline anhydrate (1). For example, to enhance the therapeutic efficacy of crystalline anhydrate (1), crystalline anhydrate (1) or a pharmaceutical composition comprising crystalline anhydrate (1) may be co-administered with one or more active agents to increase the absorption or diffusion of crystalline anhydrate (1) from the gastrointestinal tract to the systemic circulation, or to inhibit degradation of crystalline anhydrate (1) in the blood of a patient. A pharmaceutical composition comprising crystalline anhydrate (1) may be co-administered with an active agent having pharmacological effects that enhance the therapeutic efficacy of crystalline anhydrate (1).

Crystalline anhydrate (1) may be administered together with another therapeutic compound, where crystalline anhydrate (1) enhances the efficacy of the other therapeutic compound. For example, the other therapeutic compound can be an antibiotic such as a β-lactam antibiotic, and crystalline anhydrate (1), which provides systemic avibactam, can enhance the efficacy of the β-lactam antibiotic by inhibiting the hydrolysis of the β-lactam ring by β-lactamases.

Crystalline anhydrate (1) and compositions provided by the present disclosure can be administered in combination with an antibiotic such as a β-lactam antibiotic.

Antibiotics include, for example, aminoglycosides such as amikacin, gentamicin, neomycin, streptomycin, and tobramycin; β-lactams (cephalosporins, first generation) such as cefadroxil, cefazolin, cephalexin; β-lactams (cephalosporins, second generation) such as cefaclor, cefotetan, cefoxitin, cefprozil, and cefuroxime; β-lactams (cephalosporins, third generation) such as cefotaxime, cefpodoxime, ceftazidime, ceftibuten, and ceftriaxone; β-lactams (cephalosporins, sixth generation) such as cefepime; β-lactams (cephalosporins, fifth generation) such as ceftaroline; β-lactams (penicillins) such as amoxicillin, ampicillin, dicloxacillin, nafcillin, and oxacillin, penicillin G, penicillin G benzathine, penicillin G procaine, piperacillin, and ticarcillin; β-lactam monobactams such as avibactam; β-lactam carbapenems such as ertapenem, imipenem, meropenem, and doripenem; fluoroquiniolones such as ciprofloxacin, gemifloxacin, levofloxacin, moxifloxacin, norfloxacin, and ofloxacin; macrolides such as azithromycin, clarithromycin, erythromycin, fidaxomicin, lactobionate, gluceptate, and telithromycin; sulfonamides such as sulfisoxazole, sulfamethizole, sulfamethoxazole, and trimethoprim; tetracyclines such as doxycycline, minocycline, tetracycline, and tigecycline; and other antibiotics such as clindamycin, chlorramphenicol, colistin (poloymyxin E), dalbavancin, daptomycin, fosfomycin, linezolid, metronidazole, nitrofurantoin, oritavancin, quinupristin, dalfoprisin, rifampin, rifapentine, tedizolid, telavancin, and vancomycin. The antibiotic can be ceftazidime. The antibiotic can be ceftibuten.

Other examples of antibiotics that can be co-administered with crystalline anhydrate (1) include penicillins such as aminopenicillins including amoxicillin and ampicillin, anti-pseudomonal penicillins including carbenicillin, peperacillin, and ticarcillin, β-lactamase inhibitors including amoxicillin, ampicillin, piperacillin, and clavulanate, natural penicillins including penicillin g benzathine, penicillin v potassium, and procaine penicillin, and penicillinase resistant penicillin including oxacillin, dicloxacillin, and nafcillin; tetracyclines; cephalosporins such as avibactam, tazobactam, cefadroxil, defazolin, cephalexin, and cefazolin; quinolones such as lomefloxacin, ofloxacin, norfloxacin, gatifloxacin, ciprofloxacin, moxifloxacin, levofloxacin, gemifloxacin, delafoxacin, cinoxacin, nalidixic acid, trovafloxacin, and sparfloxacin; lincomycins such as lincomycin and clindamycin; macrolides such as detolides including telithromycin and macrolides such as erythromycin, azithromycin, clarithromycin, and fidaxomicin; sulfonamides such as sulfamethoxazole/trimethoprim, sulfisoxazole; glycopeptides; aminoglycosides such as paromomycin, tobramycin, gentamycin, amikacin, kanamycin, and neomycin; and carbapenems such as doripenem, meropenem, ertapenem, and cilastatin/imipenem.

Examples of suitable β-lactam antibiotics that can be co-administered with crystalline anhydrate (1) include penams such as β-lactamase-sensitive penams such as benzathine penicillin, benzylpenicillin, phenoxymethyl penicillin, and procain penicillin; β-lactamase-resistant penams such as cloxacillin, dicloxacillin, flucloxacillin, methicillin, nafcillin, oxacillin, and temocillin; broad spectrum penams such as amoxicillin and ampicillin; extended-spectrum penams such as mecillanam; carboxypenicillins such as carbenicillin and ticarcillin, and ureidopenicillins such as azlocillin, mezlocillin, and peperacillin.

Examples of suitable β-lactam antibiotics that can be co-administered with crystalline anhydrate (1) include cephams such as first generation cephams including cefazolin, cephalexin, cephalosporin C, cephalothin; second generation cephams such as cefaclor, cefamoandole, cefuroxime, cefotetan, and cefoxitin; third generation cephams such as cefixime, cefotaxime, cefpodoxime, ceflazidime, and ceftriaxone; fourth generation cephams such as cefipime and cefpirome; and fifth generation cephams such as ceftaroline.

Examples of suitable β-lactam antibiotics that can be co-administered with crystalline anhydrate (1) include carbapenems and penems such as biapenem, doripenem, ertapenem, faropenem, imipenem, meropenem, panipernem, razupenem, tebipenem, and thienamycin.

Examples of suitable β-lactam antibiotics that can be co-administered with crystalline anhydrate (1) include monobactams such as ceftibuten, aztreonam, tigemonam, nocardicin A, and tabtoxinine β-lactam.

A suitable β-lactam antibiotic can comprise ceftibuten including cis-ceftibuten and/or trans-ceftibuten.

Ceftibuten, (6R,7R)-7-((Z)-2-(2-amino-4-thiazolyl)-4-carboxycrotonamido)-8-oxo-5-thia-1-azabicyclo(4.2.0)oct-2-ene-2-carboxylic acid, is a third-generation cephalosporin antibiotic. Ceftibuten is used to treat bacterial infections such as upper or lower respiratory tract infections, urinary tract infections, intra-abdominal infections, and skin infections. Ceftibuten includes the cis and trans isomers, which exhibits about one-eighth the antibiotic activity of the cis isomer. Ceftibuten can be provided as a pharmaceutically acceptable salt, hydrate, solvate, or combination of any of the foregoing. Pharmaceutically acceptable salts of ceftibuten include, for example, the dihydrate salt.

Oral ceftibuten, as a single agent, is currently approved in the U.S. for the treatment of bacterial infections such as acute bacterial exacerbations of chronic bronchitis, acute bacterial otitis media, and pharyngitis and tonsillitis. For example, ceftibuten alone is approved for clinical use at a dose of 200 mg and 400 mg a day (once daily (QD)).

Pharmaceutical compositions provided by the disclosure comprise ceftibuten and crystalline anhydrate (1) that when orally administered provide a therapeutically effective amount of ceftibuten and avibactam in the systemic circulation of a patient such as at the site of the bacterial infection for treating a bacterial infection such as a bacterial infection caused by bacteria that produce a β-lactamase enzyme.

Methods provided by the present disclosure include methods of treating a bacterial infection in a patient comprising orally administering to a patient in need of such treatment a therapeutically effective amount of ceftibuten or pharmaceutically acceptable salt thereof and crystalline anhydrate (1).

Crystalline anhydrate (1) and pharmaceutical compositions provided by the present disclosure can be administered with β-lactamase inhibitors and/or carbapenemase inhibitors or pharmaceutical compositions thereof. Examples of suitable β-lactamase inhibitors and/or carbapenemase inhibitors include clavulanic acid, sulbactam, avibactam, tazobactam, relebactam, vaborbactam, ETX 2514, RG6068 (i.e., OP0565) (Livermore et al., *J AntiMicrob Chemother* 2015, 70: 3032) and RPX7009 (Hecker et al., *J Med Chem* 2015 58: 3682-3692).

Crystalline anhydrate (1) and pharmaceutical compositions thereof can be used to treat mycobacterial infections.

Mycobacteria are naturally resistant to most β-lactams because the presence of β-lactamases and the permeability barrier of the cell wall. Story-Roller, et al., *Front Microbiol.* 2018 9:2273. A limited number of IV β-lactams are used for therapy of non-tuberculous mycobacteria NTM). Floto, et al., Thorax. 2016 71:88-90. For example, cefoxitin or imipenem are used for the treatment of infections caused by *M. abscessus* because these antibiotics are stable to hydrolysis by mycobacterial β-lactamases. Therapy using β-lactam antibiotics is lengthy, with a recommended initial treatment phase of up to 12 weeks and requires an intravenous (IV) infusion several times per day. A maintenance phase of treatment can extend to one year or longer. Floto et al., Id. There are no oral β-lactam antibiotics available to treat NTM because none of the orally available β-lactam antibiotics are sufficiently potent. For example, the minimal inhibitory concentration (MIC) of NTM to amoxicillin, an IV oral antibiotic, is often well above the concentrations reached at the site of the infection after oral administration, which precludes clearing the infection.

Crystalline anhydrate (1) can be used in combination with amoxicillin to treat bacterial infections.

Pharmaceutical compositions provided by the disclosure comprise amoxicillin and crystalline anhydrate (1) that when orally administered provide a therapeutically effective amount of amoxicillin and avibactam in the plasma of a patient for treating a bacterial infection such as a mycobacterial infection.

Methods provided by the present disclosure include methods of treating a mycobacterial infection in a patient comprising orally administering to a patient in need of such treatment a therapeutically effective amount of amoxicillin or a pharmaceutically acceptable salt thereof and crystalline anhydrate (1).

Amoxicillin is in the class of β-lactam antibiotics. Amoxicillin, (1S,4S,7S)-7-((R)-2-amino-2-(4-hydroxyphenyl)acetamido)-3,3-dimethyl-2-thia-6-azabicyclo[3.2.0]heptane-4-carboxylic acid, has the structure:

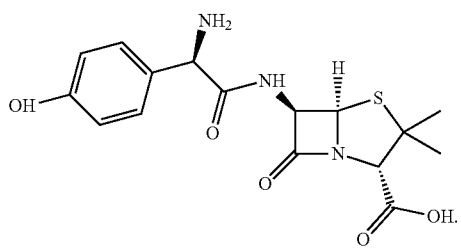 [SMILES: CC1(C)S[C@@H]2[C@H](NC(=O)[C@H](N)c3ccc(O)cc3)C(=O)N2[C@H]1C(=O)O]

β-lactams act by binding to penicillin-binding proteins that inhibit a process called transpeptidation, leading to activation of autolytic enzymes in the bacterial cell wall. This process leads to lysis of the cell wall, and thus, the destruction of the bacterial cell. This type of activity is referred to as bactericidal killing.

Amoxicillin is used to treat infections caused by Gram-positive bacteria and Gram-negative bacteria including most *Streptococcus* species including *Listeria monocytogenes*, *Enterococcus*, *Haemophilus influenzae*, some *Escherichia coli*, *Actinomyces*, Clostridial species, *Salmonella*, *Shigella*, and *Corynebacteria*.

Amoxicillin is FDA approved for the treatment of genitourinary tract infections, ear, nose, and throat infections, lower respiratory tract infections, *Helicobacter pylori* infections, pharyngitis, tonsillitis, and skin and skin structure infections. Amoxicillin is recommended as the first-line treatment by the Infectious Disease Society of America (IDSA), for acute bacterial rhinosinusitis and as one of the treatments for community-acquired pneumonia.

Crystalline anhydrate (1) can be used in combination with a β-lactam antibiotic such as amoxicillin to treat bacterial infections in a patient such as Actinomycetales bacterial infections. Actinomycetales is an order of Gram-positive bacteria with complex cell wall structures. Actinomycetales has three major families of pathogens: Mycobacteriaceae, Actinomycetaceae, and Nocardiaceae.

The genus *Mycobacterium* genus includes *M. tuberculosis*, *M. bovis*, *M. africanum*, *M. leprae*, and non-tuberculous mycobacteria. Non-tuberculous mycobacteria include *M. arupense*, *M. avium*, *M. asiaticum*, *M. bohemicum*, *M. branderi*, *M. chemaera*, *M. selatum*, *M. conspicuum*, *M. doricum*, *M. florentinum*, *M. genavense*, *M. haemophilum*, *M. heckeshornense*, *M. heidelbergense*, *M. intermedium*, *M. interjectum*, *M. intracellulare*, *M. kansasii*, *M. kubicae*, *M. lacus*, *M. lentiflavum*, *M. malmoense*, *M. marinum*, *M. nebraskense*, *M. parmense*, *M. parascrofulaceum*, *M. palustre*, *M. saskatchewanse*, *M. scrofulaceum*, *M. selatum*, *M. sherrissii*, *M. shottsii*, *M. shimodei*, *M. simiae*, *M. szulgai*, *M. tusciae*, *M. triplex*, *M. ulcerans*, *M. xenopi*, *M. abscessus*, *M. chelonae*, *M. fortuitum*, *M. mucogenicum*, *M. peregrinum*, *M. porcinum*, *M. senegalense*, *M. alvei*, *M. boenickei*, *M. bollettii*, *M. brumae*, *M. canariasense*, *M. confluentis*, *M. cosmeticum*, *M. elephantis*, *M. goodii*, *M. hassiacum*, *M. holsaticum*, *M. immunogenum*, *M. mageritence*, *M. novocastrense*, *M. phocaicum*, *M. septicum*, *M. smegmatis*, *M. thermoresistible*, *M. wolinskyi*. The genus Actinomycetes includes *A. israelii*, *A. meyeri*, *A. naeslundii*, *A. odontolyticus*, and *A. viscosus*. The genus *Nocardia* includes several pathogenic species including N. asteroids, *N. abscessus*, *N. brasiliensis*, *N. cyriacigeorgica*, *N. farcinica*, *N. nova*, *N. otitidiscaviarum*, and *N. veterana*.

A combination of an orally administered β-lactam antibiotic such as amoxicillin and crystalline anhydrate (1) can be used to treat a bacterial infection caused by a bacteria of the genus Mycobacteriaceae.

A combination of orally administered amoxicillin and crystalline anhydrate (1) can be used to treat an infection caused by *M. ulcerans*.

A combination of orally administered amoxicillin and crystalline anhydrate (1) can be used to treat an infection caused by the *M. abscessus* complex. The *M. abscessus* complex can cause pulmonary disease, especially in vulnerable hosts with underlying structural lung disease, such as cystic fibrosis, bronchiectasis, and prior tuberculosis.

A combination of orally administered amoxicillin and crystalline anhydrate (1) can be used to treat a non-tuberculous mycobacterial infection is caused by a non-tuberculous *mycobacterium* such as, for example, *M. avium*, *M. intracellulare*, *M. kansasii*, *M. xenopi*, *M. marinum*, *M. malmoense*, *M. simiae*, *M. abscessus*, *M. ulcerans*, *M. chelonae*, *M. fortuitum*, or a combination of any of the foregoing.

A combination of orally administered amoxicillin and crystalline anhydrate (1) can be used to treat a MAC infection caused by *M. avium* and *M. intracellulare*.

A combination of orally administered amoxicillin and crystalline anhydrate (1) can be used to treat a pulmonary infection, a soft tissue infection, a central nervous system infection, bacteremia, an ocular infection, or a combination of any of the foregoing.

Crystalline anhydrate (1) can be co-administered with a β-lactamase inhibitor derivative that exhibits oral bioavailability of the corresponding β-lactamase inhibitor. Examples of suitable derivatives of β-lactamase inhibitors that provide oral bioavailability of the corresponding β-lactamase inhibitor include derivatives of avibactam, derivatives of relebactam, and derivatives of nacubactam, as described, for example, in U.S. Pat. No. 10,085,999, which is incorporated by reference in its entirety. Orally bioavailable derivatives of relebactam and nacubactam are disclosed in U.S. application Ser. No. 16/589,498, filed on Oct. 1, 2019, which is incorporated by reference in its entirety.

Derivatives of avibactam, derivatives of relebactam, or derivatives of nacubactam can have the structure of Formula (2):

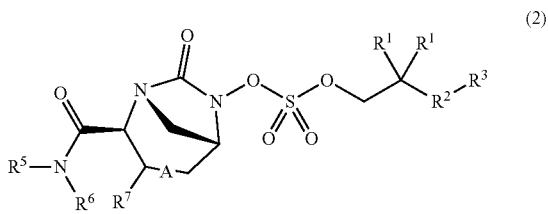

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (–) and $R^7$ is hydrogen, or A is a double bond (=) and $R^7$ is $C_{1-3}$ alkyl.

Derivatives of avibactam, derivatives of relebactam, or derivatives of nacubactam encompassed by the structure of Formula (2) can include pharmaceutically acceptable salts thereof.

A relebactam derivative can have the structure of Formula (3):

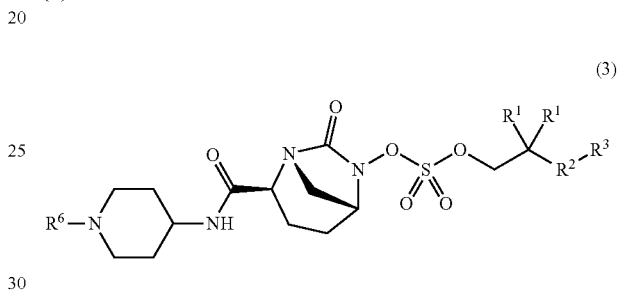

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^6$ is selected from a moiety of Formula (6a), a moiety of Formula (6b), a moiety of Formula (6c), and a moiety of Formula (6d):

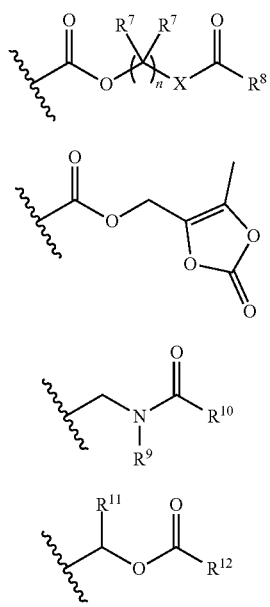

wherein,
each $R^7$ is independently selected from hydrogen, $C_{1-8}$ alkyl, or each $R^7$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;
n is an integer from 1 to 4;
X is selected from O and NH;
$R^8$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;
$R^9$ is selected from hydrogen and $C_{1-6}$ alkyl;
$R^{10}$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; $C_{1-6}$ alkyl;
$R^{11}$ is selected from hydrogen and $C_{1-6}$ alkyl; and
$R^{12}$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Relebactam derivatives can comprise a pharmaceutically acceptable salt of a compound of Formula (3).

A nacubactam derivative can have the structure of Formula (4):

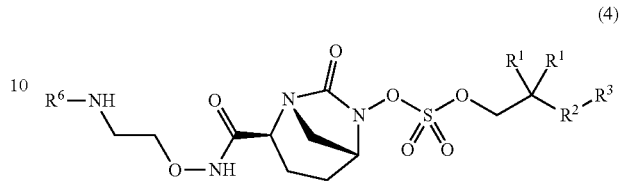

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^6$ is selected from a moiety of Formula (6a), a moiety of Formula (6b), a moiety of Formula (6c), and a moiety of Formula (6d):

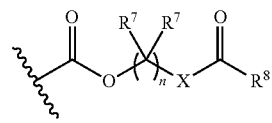

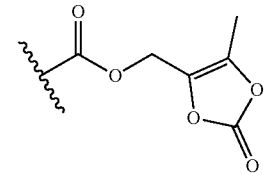

-continued

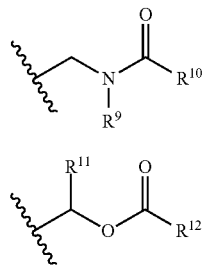

(6c)

(6d)

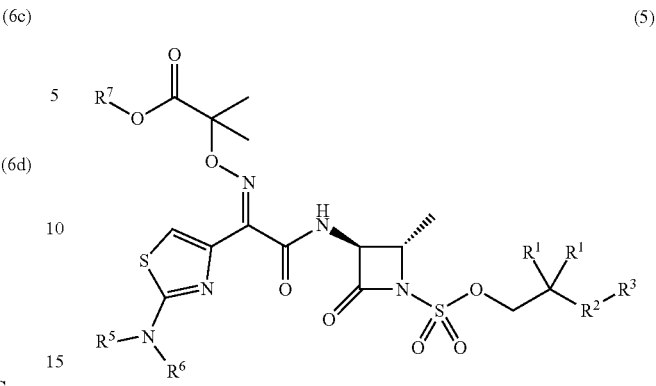

(5)

wherein, each $R^7$ is independently selected from hydrogen, $C_{1-8}$ alkyl, or each $R^7$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

n is an integer from 1 to 4;

X is selected from O and NH;

$R^8$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^9$ is selected from hydrogen and $C_{1-6}$ alkyl;

$R^{10}$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; $C_{1-6}$ alkyl;

$R^{11}$ is selected from hydrogen and $C_{1-6}$ alkyl; and $R^{12}$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Nacubactam derivatives can comprise a pharmaceutically acceptable salt of a compound of Formula (4).

Crystalline anhydrate (1) can be co-administered with an aztreonam derivative as disclosed in U.S. Pat. No. 10,280,161, filed on Oct. 1, 2018, which is incorporated by reference in its entirety. Aztreonam is a monobactam antibiotic used primarily to treat gram-negative bacteria. The derivatives disclosed in U.S. Pat. No. 10,280,161, when administered orally, provide increased oral bioavailability of aztreonam compared to orally administered aztreonam, which is incorporated by reference in its entirety. Aztreonam derivatives can have the structure of Formula (5):

or a pharmaceutically acceptable salt thereof, wherein, each $R^1$ is independently selected from $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^7$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl.

An aztreonam derivative can comprise a pharmaceutically acceptable salt of a compound of Formula (5).

In compounds of Formula (5), each substituent can be independently selected from —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl.

In compounds of Formula (5), each of R$^5$, R$^6$, and R$^7$ can be hydrogen.

In compounds of Formula (5), each of R$^5$ and R$^6$ can be hydrogen; and R$^7$ can be selected from hydrogen, C$_{1-6}$ alkyl, C$_{1-6}$ heteroalkyl, and 4-(yl-methyl)-5-methyl-1,3-dioxol-2-one.

In compounds of Formula (5), each R$^1$ can be independently C$_{1-6}$ alkyl, or each R$^1$ together with the geminal carbon atom to which each R$^1$ is bonded form a C$_{3-6}$ cycloalkyl ring or a substituted C$_{3-6}$ cycloalkyl ring.

In compounds of Formula (5), R$^2$ can be selected from a single bond, C$_{1-6}$ alkyl, C$_{1-2}$ alkanediyl, and substituted C$_{1-2}$ alkanediyl.

In compounds of Formula (5), R$^3$ can be selected from —O—C(O)—R$^4$, —C(O)—O—R$^4$, —S—C(O)—R$^4$, —C(O)—S—R$^4$, —S—S—R$^4$, —NH—R$^4$, and —CH(—NH$_2$)(—R$^4$); where R$^4$ is defined as for Formula (1), or each R$^4$ can be selected from hydrogen and C$_{1-8}$ alkyl.

In compounds of Formula (5), R$^3$ can be —C(O)—O—R$^4$, and R$^4$ can be selected from hydrogen and C$_{1-8}$ alkyl.

In compounds of Formula (5), R$^3$ can be —C(O)—O—R$^{4'}$ wherein R$^4$ can be selected from C$_{1-8}$ alkyl, C$_{1-8}$ heteroalkyl, C$_{5-7}$ cycloalkyl, C$_{5-7}$ heterocycloalkyl, C$_6$ aryl, C$_{7-9}$ arylalkyl, substituted C$_{1-8}$ alkyl, substituted C$_{1-8}$ heteroalkyl, substituted C$_{5-6}$ cycloalkyl, substituted C$_{5-6}$ heterocycloalkyl, substituted C$_6$ aryl, and C$_{7-9}$ arylalkyl.

In compounds of Formula (5), R$^2$ can be a single bond; R$^3$ can be C$_{1-3}$ alkyl; each R$^1$ together with the carbon atom to which each R$^1$ is bonded form a C$_{4-6}$ heterocycloalkyl ring or a substituted C$_{4-6}$ heterocycloalkyl ring each of R$^5$ and R$^6$ can be hydrogen; and R$^7$ can be selected from hydrogen, C$_{1-6}$ alkyl, C$_{1-6}$ heteroalkyl, and 4-(yl-methyl)-5-methyl-1,3-dioxol-2-one.

In compounds of Formula (5), each R$^1$ can be methyl; R$^2$ can be selected from a single bond, methanediyl, ethanediyl, —CH(—OH)—, —CH(—O—C(O)—CH$_2$CH$_3$)—, and 1,2-benzene-diyl; R$^3$ can be selected from —O—C(O)—R$^4$, —C(O)—O—R$^4$, —S—C(O)—R$^4$, —C(O)—S—R$^4$, —S—S—R$^4$, —NHR$^4$, and —CH(—NH$_2$)(—R$^4$), wherein R$^4$ can be selected from C$_{1-8}$ alkyl, C$_{1-8}$ heteroalkyl, C$_{7-9}$ arylalkyl, and C$_{5-7}$ heterocycloalkyl; each of R$^5$ and R$^6$ can be hydrogen; and R$^7$ can be selected from hydrogen, C$_{1-6}$ alkyl, C$_{1-6}$ heteroalkyl, and 4-(yl-methyl)-5-methyl-1,3-dioxol-2-one.

In compounds of Formula (5), each R$^1$ can be methyl; R$^2$ can be selected from a single bond, methanediyl, ethanediyl, —CH(—OH)—, —CH(—O—C(O)—CH$_2$CH$_3$)—, and 1,2-benzene-diyl; R$^3$ can be selected from —C(O)—O—R$^4$, wherein R$^4$ can be selected from C$_{1-8}$ alkyl, C$_{1-8}$ heteroalkyl, C$_{7-9}$ arylalkyl, and C$_{5-7}$ heterocycloalkyl; each of R$^5$ and R$^6$ can be hydrogen; and R$^7$ can be selected from hydrogen, C$_{1-6}$ alkyl, C$_{1-6}$ heteroalkyl, and 4-(yl-methyl)-5-methyl-1,3-dioxol-2-one.

In compounds of Formula (5), each R$^1$ can be methyl; R$^2$ can be selected from a single bond, methanediyl, ethanediyl, —CH(—OH)—, —CH(—O—C(O)—CH$_2$CH$_3$)—, and 1,2-benzene-diyl; R$^3$ can be selected from —O—C(O)—R$^4$, —C(O)—O—R$^4$, —S—C(O)—R$^4$, —C(O)—S—R$^4$, —S—S—R$^4$, —NHR$^4$, and —CH(—NH$_2$)(—R$^4$), wherein R$^4$ can be selected from methyl, ethyl, n-propyl, can be isopropyl, n-butyl, sec-butyl can isobutyl, tert-butyl, 2-methoxyethyl, methylbenzene, oxetane-3-oxy-yl, cyclopentyl, cyclohexyl, and 2-pyrrolidinyl; each of R$^5$ and R$^6$ can be hydrogen; and R$^7$ can be selected from hydrogen, C$_{1-6}$ alkyl, C$_{1-6}$ heteroalkyl, and 4-(yl-methyl)-5-methyl-1, 3-dioxol-2-one.

In compounds of Formula (5), each R$^1$ can be methyl; R$^2$ can be selected from a single bond, methanediyl, ethanediyl, —CH(—OH)—, —CH(—O—C(O)—CH$_2$CH$_3$)—, and 1,2-benzene-diyl; R$^3$ can be selected from —C(O)—O—R$^4$, wherein R$^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl; each of R$^5$ and R$^6$ can be hydrogen; and R$^7$ can be selected from hydrogen, C$_{1-6}$ alkyl, C$_{1-6}$ heteroalkyl, and 4-(yl-methyl)-5-methyl-1,3-dioxol-2-one.

In compounds of Formula (5), each R$^1$ can be independently C$_{1-3}$ alkyl; each R$^2$ can be a single bond; and each of R$^5$, R$^6$, and R$^7$ can be hydrogen.

In compounds of Formula (5), each R$^1$ can be methyl; R$^2$ can be a single bond; R$^3$ can be —C(O)—O—R$^4$, wherein R$^4$ can be selected from C$_{1-10}$ alkyl, C$_{1-10}$ heteroalkyl, C$_{7-10}$ alkylarene, and C$_{5-10}$ heteroalkylcycloalkyl; each of R$^5$ and R$^6$ can be hydrogen; and R$^7$ can be selected from hydrogen, C$_{1-6}$ alkyl, C$_{1-6}$ heteroalkyl, and 4-(yl-methyl)-5-methyl-1, 3-dioxol-2-one.

In compounds of Formula (5), each R$^1$ can be selected from C$_{1-6}$ alkyl; R$^4$ can be selected from C$_{1-6}$ alkyl, C$_{1-6}$ heteroalkyl, C$_{5-6}$ cycloalkyl, and C$_{5-6}$ heterocycloalkyl; each of R$^5$ and R$^6$ can be hydrogen; and R$^7$ can be selected from hydrogen, C$_{1-6}$ alkyl, C$_{1-6}$ heteroalkyl, and 4-(yl-methyl)-5-methyl-1,3-dioxol-2-one.

A compound of Formula (5) can be selected from:

2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene) amino)oxy)-2-methylpropanoic acid;

2-((((E)-1-(2-aminothiazol-4-yl)-2-(((2S,3S)-1-((3-ethoxy-2,2-dimethyl-3-oxopropoxy)sulfonyl)-2-methyl-4-oxoazetidin-3-yl)amino)-2-oxoethylidene)amino)oxy)-2-methylpropanoic acid;

2-((((E)-1-(2-aminothiazol-4-yl)-2-(((2S,3S)-1-((2,2-dimethyl-3-oxo-3-propoxypropoxy)sulfonyl)-2-methyl-4-oxoazetidin-3-yl)amino)-2-oxoethylidene)amino)oxy)-2-methylpropanoic acid;

methyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;

ethyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;

propyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;

methyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;

ethyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;

propyl 3-(((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;

methyl 3-(((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;

ethyl 3-(((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;

propyl 3-(((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;

a pharmaceutically acceptable salt of any of the foregoing; and a combination of any of the foregoing.

A compound of Formula (5) can have the structure of Formula (5a), wherein each $R^1$ can be independently $C_{1-6}$ alkyl; $R^2$ can be a single bond; $R^3$ can be —C(O)—O—$R^4$, wherein $R^4$ can be selected from $C_{1-10}$ alkyl, $C_{1-10}$ heteroalkyl, $C_{7-10}$ alkylarene, and $C_{5-10}$ heteroalkylcycloalkyl; each of $R^5$ and $R^6$ can be hydrogen; and $R^7$ can be selected from hydrogen, $C_{1-6}$ alkyl, $C_{1-6}$ heteroalkyl, and 4-(yl-methyl)-5-methyl-1,3-dioxol-2-one.

In compounds of Formula (5a), each $R^1$ can be independently $C_{1-3}$ alkyl.

In compounds of Formula (5a), each $R^1$ can be methyl

In compounds of Formula (5a), $R^4$ can be selected from $C_{1-6}$ alkyl and $C_{1-6}$ heteroalkyl.

In compounds of Formula (5a), $R^4$ can be selected from methyl, ethyl, and n-propyl.

In compounds of Formula (5a), $R^7$ can be hydrogen.

In compounds of Formula (5a), $R^7$ can be $C_{1-6}$ alkyl.

In compounds of Formula (5a), $R^7$ can be 4-(yl-methyl)-5-methyl-1,3-dioxol-2-one, which has the structure:

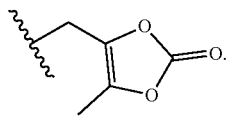 [SMILES: *Cc1oc(=O)oc1C]

In compounds of Formula (5a), each $R^1$ can be methyl; $R^3$ can be —C(O)—O—$R^4$, wherein $R^4$ can be selected from $C_{1-3}$ alkyl; and $R^7$ can be selected from hydrogen, $C_{1-6}$ alkyl, $C_{1-6}$ heteroalkyl, and 4-(yl-methyl)-5-methyl-1,3-dioxol-2-one.

A compound of Formula (5a) can be 2-((((E)-1-(2-aminothiazol-4-yl)-2-(((2S,3S)-1-(((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid, or a pharmaceutically acceptable salt thereof.

A compound of Formula (5a) can be methyl 3-(((((2S,3S)-3-((E)-2-(2-aminothiazol-4-yl)-2-(((2-methyl-1-((5-methyl-2-oxo-1,3-dioxolan-4-yl)methoxy)-1-oxopropan-2-yl)oxy)imino)acetamido)-2-methyl-4-oxoazetidin-1-yl)sulfonyl)oxy)-2,2-dimethylpropanoate, or a pharmaceutically acceptable salt thereof.

A compound of Formula (5a) can be methyl 3-(((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate, or a pharmaceutically acceptable salt thereof.

A compound of Formula (5a) can be methyl 3-(((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate, or a pharmaceutically acceptable salt thereof.

A compound of Formula (5a) can be methyl 3-(((((2S,3S)-3-((E)-2-(2-aminothiazol-4-yl)-2-(((2-methyl-1-oxo-1-propoxypropan-2-yl)oxy)imino)acetamido)-2-methyl-4-oxoazetidin-1-yl)sulfonyl)oxy)-2,2-dimethylpropanoate, or a pharmaceutically acceptable salt thereof.

A compound of Formula (5a) can be 2-((((E)-1-(2-aminothiazol-4-yl)-2-(((2S,3S)-1-(((3-ethoxy-2,2-dimethyl-3-oxopropoxy)sulfonyl)-2-methyl-4-oxoazetidin-3-yl)amino)-2-oxoethylidene)amino)oxy)-2-methylpropanoic acid, or a pharmaceutically acceptable salt thereof.

A compound of Formula (5a) can be ethyl 3-(((((2S,3S)-3-((E)-2-(2-aminothiazol-4-yl)-2-(((2-methyl-1-((5-methyl-2-oxo-1,3-dioxolan-4-yl)methoxy)-1-oxopropan-2-yl)oxy)imino)acetamido)-2-methyl-4-oxoazetidin-1-yl)sulfonyl)oxy)-2,2-dimethylpropanoate, or a pharmaceutically acceptable salt thereof.

A compound of Formula (5a) can be ethyl 3-(((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate, or a pharmaceutically acceptable salt thereof.

A compound of Formula (5a) can be ethyl 3-(((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate.

A compound of Formula (5a) can be ethyl 3-(((((2S,3S)-3-((E)-2-(2-aminothiazol-4-yl)-2-(((2-methyl-1-oxo-1-propoxypropan-2-yl)oxy)imino)acetamido)-2-methyl-4-oxoazetidin-1-yl)sulfonyl)oxy)-2,2-dimethylpropanoate, or a pharmaceutically acceptable salt thereof.

Methods of synthesizing aztreonam derivatives are disclosed in U.S. Provisional Application No. 62/838,880, filed on Apr. 25, 2019, which is incorporated by reference in its entirety.

It should be understood that any suitable combination of the compounds and pharmaceutical compositions provided herein with one or more of the above therapeutic agents and optionally one or more further pharmacologically active substances are considered to be within the scope of the present disclosure. In some embodiments, the compounds and pharmaceutical compositions provided by the present disclosure are administered prior to or subsequent to the one or more additional active ingredients.

ASPECTS OF THE INVENTION

The invention is further defined by the following aspects.

Aspect 1. The compound, crystalline ethyl 3-((((((1R,2S,5R)-2-carbamoyl-7-oxo-1,6-diazabicyclo[3.2.1]octan-6-yl)oxy)sulfonyl)oxy)-2,2-dimethylpropanoate anhydrate characterized by an X-ray powder diffraction (XRPD) pattern having characteristic scattering angles (2θ) at least at 3.16°±0.2°, 6.37°±0.2°, 5.38°±0.2°, and 17.35°±0.2° at a Kα2/Kα1 (0.5) wavelength.

Aspect 2. The compound of aspect 1, characterized by an XRPD pattern having characteristic scattering angles (2θ) at least at 3.16°±0.2°, 6.37°±0.2°, 5.38°±0.2°, 15.77°±0.2°, and 17.35°±0.2° at a Kα2/Kα1 (0.5) wavelength.

Aspect 3. The compound of aspect 1, characterized by an XRPD pattern having characteristic scattering angles (2θ) at least at 3.16°±0.2°, 6.37°±0.2°, 5.38°±0.2°, 12.75°±0.2°, 15.77°±0.2°, 17.35°±0.2°, 25.68°±0.2°, and 27.13°±0.2° at a Kα2/Kα1 (0.5) wavelength.

Aspect 4. The compound of any one of aspects 1 to 3, wherein the compound has a weight loss from 7.2% to 9.2% over a temperature range from 125° C. to 150° C. and does not exhibit an appreciable weight loss over a range from 30° C. to 125° C., as determined by thermogravimetric analysis (TGA).

Aspect 5. The compound of any one of aspects 1 to 4, wherein the compound exhibits a reversible moisture absorption over a range of humidity from 0% RH to 95% RH with a maximum increase in mass of about 3 wt % at 25° C./95% RH as determined using dynamic vapor sorption.

Aspect 6. The compound of any one of aspects 1 to 5, wherein the compound is storage stable during storage at 25° C./60% RH for 4 weeks.

Aspect 7. The compound of any one of aspects 1 to 6, wherein the compound exhibits a melting point from 123.0° C. to 127° C. as determined by differential scanning calorimetry.

Aspect 8. A method of treating a bacterial infection comprising administering to patient in need of such treatment a therapeutically effective amount of the compound of any one of aspects 1 to 7 and a therapeutically effective amount of a β-lactam antibiotic, wherein bacteria causing the bacterial infection produce a β-lactamase.

Aspect 9. The method of aspect 8, wherein administering comprises orally administering.

Aspect 10. An oral dosage form comprising the compound of any one of aspects 1 to 7.

Aspect 11. The oral dosage form of aspect 10, further comprising an antibiotic.

Aspect 12. The oral dosage form of aspect 11, wherein the antibiotic comprises a β-lactam antibiotic.

Aspect 13. A method of treating a bacterial infection in a patient comprising administering to a patient in need of such treatment the oral dosage form of any one of aspects 10 to 12 and a therapeutically effective amount of a β-lactam antibiotic, wherein bacteria causing the bacterial infection produce a β-lactamase.

Aspect 14. The method of aspect 13, wherein administering comprises orally administering.

Aspect 15. A pharmaceutical composition comprising the compound of any one of aspects 1 to 7 and a pharmaceutically acceptable vehicle.

Aspect 16. The pharmaceutical composition of aspect 15, further comprising an antibiotic.

Aspect 17. The pharmaceutical composition of aspect 16, wherein the antibiotic comprises a β-lactam antibiotic.

Aspect 18. A method of treating a bacterial infection in a patient comprising administering to a patient in need of such treatment a therapeutically effective mount of the pharmaceutical composition of any one of aspects 15 to 17, and a therapeutically effective amount of a β-lactam antibiotic, wherein bacteria causing the bacterial infection produce a β-lactamase.

Aspect 19. The method of aspect 18, wherein administering comprises orally administering.

Aspect 20. An oral dosage form comprising the pharmaceutical composition of any one of aspects 10 to 12.

Aspect 21. The oral dosage form of aspect 20, further comprising an antibiotic.

Aspect 22. The oral dosage form of aspect 21, wherein the antibiotic comprises a β-lactam antibiotic.

Aspect 23. A method of treating a bacterial infection in a patient comprising administering to a patient in need of such treatment a therapeutically effective mount of the oral dosage form of any one of aspects 20 to 22, and a therapeutically effective amount of a β-lactam antibiotic, wherein bacteria causing the bacterial infection produce a β-lactamase.

Aspect 24. The method of aspect 23, wherein administering comprises orally administering.

Aspect 25. A method of preparing the compound of any one of aspects 1 to 7, comprising: dissolving ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate in a mixture of ethyl acetate, water, and n-heptane to form a triphasic mixture; and precipitating crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate from the triphasic mixture.

Aspect 26. The method of aspect 25, wherein the mixture comprises 6.5 volumes of ethyl acetate, 10.5 volumes of water, and 13 volumes of n-heptane for each one volume of ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate.

Aspect 27. The method of any one of aspects 25 to 26, further comprising, before precipitating, heating the mixture has a temperature from 35° C.±5° C. while stirring for at least 1 hour.

Aspect 28. The method of any one of aspects 25 to 27, wherein precipitating comprises: storing the triphasic mixture for from 15 min to 30 min; cooling the triphasic mixture to 5° C.±5° C. over a period of at least 3 hours; and stirring the triphasic mixture at to 5° C.±5° C. for at least 1 h.

Aspect 29. The method of any one of aspects 25 to 28, further comprising, after precipitating, filtering, washing, and drying the precipitated crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate.

Aspect 30. A method of treating a bacterial infection in a patient comprising administering to a patient in need of such treatment a therapeutically effective amount of the compound of any one of claims 1 to 7 and a therapeutically effective amount of a β-lactam antibiotic, wherein a combination of avibactam and the β-lactam antibiotic is effective in treating the bacterial infection.

Aspect 31. The method of claim 30, wherein administering the compound of any one of claims 1 to 7 comprises orally administering.

Aspect 32. The method of any one of claims 30 to 31, wherein administering the β-lactam antibiotic comprises orally administering.

Aspect 33. The method of any one of aspects 30 to 32, wherein the β-lactam antibiotic comprises amoxicillin.

Aspect 34. The method of any one of aspects 30 to 32, wherein the β-lactam antibiotic comprises ceftibuten.

Aspect 35. The method of any one of aspects 30 to 32, wherein the β-lactam antibiotic comprises an aztreonam derivative of Formula (5).

Aspect 36. The pharmaceutical composition of aspect 17, wherein the β-lactam antibiotic comprises amoxicillin.

Aspect 37. The pharmaceutical composition of aspect 17, wherein the β-lactam antibiotic comprises ceftibuten.

Aspect 38. The pharmaceutical composition of aspect 17, wherein the β-lactam antibiotic comprises an aztreonam derivative of Formula (5).

Aspect 39. A method of treating a bacterial infection in a patient comprising administering to a patient in need of such treatment a therapeutically effective mount of the pharmaceutical composition of any one of aspects 36 to 38, wherein bacteria causing the bacterial infection produce a β-lactamase.

Aspect 40. An oral dosage form comprising the compound of any one of aspects 1 to 7 and a β-lactam antibiotic, wherein the β-lactam antibiotic comprises amoxicillin, ceftibuten, aztreonam derivative of Formula (5), or a combination of any of the foregoing.

Aspect 41. An oral dosage form comprising the pharmaceutical composition of any one of aspects 36 to 38.

Aspect 42. A method of treating a bacterial infection in a patient comprising administering to a patient in need of such treatment a therapeutically effective mount of the oral dosage form of any one of aspects 40 and 41, wherein bacteria causing the bacterial infection produce a β-lactamase.

EXAMPLES

The following examples describe the synthesis of ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate and the preparation and properties of crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate. It will be apparent to those skilled in the art that many modifications, both to materials and methods, may be practiced without departing from the scope of the disclosure.

Example 1

Synthesis of Ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate Step 1. Synthesis of (1R,2S,5R)-6-hydroxy-7-oxo-1,6-diazabicyclo[3.2.1]octane-2-carboxamide

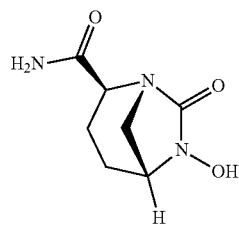

A stirred mixture of (1R,2S,5R)-6-(benzyloxy)-7-oxo-1,6-diazabicyclo[3.2.1]octane-2-carboxamide (550 mg, 2.0 mmol), palladium on carbon (10% by weight; 340 mg, 0.3 mmol) and MeOH (18 mL) was hydrogenated under 1 atm (balloon) until analysis by thin-layer chromatography (TLC) indicated completion of the reaction (approximately, 30 min; reaction monitored by TLC using MeOH/CH$_2$Cl$_2$ 5:95 as eluent). The mixture was filtered through a pad of Celite and the pad was rinsed thoroughly with MeOH (ca. 20 mL). The filtrate was concentrated under vacuum (water bath temperature not exceeding 25° C.) to give the product as a clear and colorless oil. The oil was dried under vacuum for 1 h, and the residue was used immediately in the next step without further purification. Yield assumed quantitative. LC-MS: m/z=186.0 [M+H]$^+$.

Step 2: Synthesis of ethyl 3-((chlorosulfonyl)oxy)-2,2-dimethylpropanoate

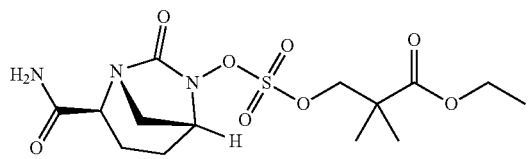

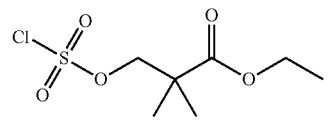

A solution of distilled sulfuryl chloride (0.55 mL, 7.5 mmol) in Et$_2$O (10 mL) was cooled to −78° C. under an argon atmosphere. A solution of ethyl 3-hydroxy-2,2-dimethylpropanoate (1.0 g, 6.8 mmol) and pyridine (0.55 mL, 6.8 mmol) in Et$_2$O (1.0 mL) was then added dropwise over 1 h via a syringe. The syringe was rinsed with Et$_2$O (3×1 mL), each rinse being added to the reaction mixture. The acetone/CO$_2$ bath was removed, and the mixture was allowed to warm to room temperature, then stirred at room temperature for 4 h. TLC analysis (EtOAc/hexanes; 3:7) did not indicate that the reaction was complete. The mixture was re-cooled to −78° C. and more SO$_2$Cl$_2$ (0.11 mL) was added, and the mixture allowed to warm to 25° C. and stirred for an additional 2 h. The mixture was filtered, and the filtrate concentrated under vacuum to give the product (yield assumed quantitative). $^1$H NMR (300 MHz, CDCl$_3$): δ 4.50 (s, 2H), 4.19 (q, J=6.9 Hz, 2H), 1.31 (s, 6H), 1.28 (t, J=6.9 Hz, 3H).

Step 2: Synthesis of ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate

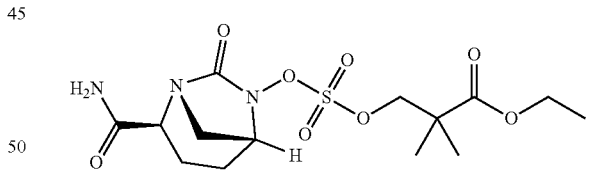

(1R,2S,5R)-6-Hydroxy-7-oxo-1,6-diazabicyclo[3.2.1]octane-2-carboxamide (Step 1) (370 mg, 2.0 mmol) was dissolved in THF (7.0 mL) and 1,3-dimethyltetrahydropyrimidin-2(1H)-one (3.0 mL) and the resulting solution was cooled to −78° C. under an argon atmosphere. A solution of NaHMDS in THF (1M; 2.2 mL, 2.2 mmol) was added dropwise, and the mixture was stirred at −78° C. for 10 min. A solution of ethyl 3-((chlorosulfonyl)oxy)-2,2-dimethylpropanoate (Step 2) (538 mg, 2.2 mmol) in THF (1 mL) was then added quickly to the reaction mixture via syringe. The syringe was rinsed with THF (3×0.5 mL), each rinse being added to the reaction mixture. After 10 min at −78° C., the reaction mixture was allowed to warm to room temperature and stirred at 25° C. until complete as determined by LC-MS and TLC analysis (ca. 2 h). EtOAc (20 mL) and saturated aqueous NaHCO$_3$ (20 mL) were added and the organic and aqueous layers were partitioned. The organic layer was washed with saturated NaHCO$_3$ (20 mL), water (3×20 mL), brine (20 mL), dried (Na$_2$SO$_4$) and concentrated under vacuum to leave a crude residue. The residue was purified by column chromatography on silica gel using EtOAc/hexanes (1:9 to 1:0) as eluent to give the product (318 mg, 39%) as a solid. LC-MS: m/z=394.1 [M+H]$^+$. $^1$H NMR (CDCl$_3$, 300 MHz): δ 6.50 (s, 1H), 5.78 (s, 1H), 4.71 (d, J=8.7 Hz, 1H), 4.59 (d, J=8.7 Hz, 1H), 4.22-4.12 (m, 3H), 4.05 (d, J=6.9 Hz, 1H), 3.34-3.30 (m, 1H), 3.01 (d, J=12.3 Hz, 1H), 2.46-2.40 (m, 1H), 2.18-2.12 (m, 1H), 2.00-1.79 (m, 2H), 1.28-1.24 (m, 9H). $^{13}$C NMR (300 MHz, CDCl$_3$): δ 174.2, 171.2, 167.1, 80.5, 61.9, 61.4, 60.2, 47.2, 42.8, 22.2, 21.7, 20.8, 17.5, 14.2.

Example 2

Crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1)

The following process was used to obtain crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1).

Crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1) was prepared by charging ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate into a 100-gallon glass-lined reactor. Purified water (USP grade) was charged to the crude solids. Ethyl acetate (urethane grade, 99.5%) was charged to the reactor and agitated. The reaction mixture was then heated to an internal temperature of 30° C. to 40° C., and then the reaction mixture was stirred for a minimum of 5 min while maintaining an internal temperature of 30° C. to 40° C. The mixture appeared hazy while stirring. To allow for greater visibility, it is recommended to temporarily stop agitation to allow the layers to separate. An additional amount of ethyl acetate (urethane grade, 99.5%) was added to the reaction mixture, and the reaction mixture was stirred for a minimum of 5 min while maintaining an internal temperature of 30° C. to 40° C. To allow for greater visibility, it is recommended to temporarily stop agitation to allow the layers to separate. Filtered n-heptane (99%) was charged to the reaction mixture over a minimum of 10 min while maintaining an internal temperature of 30° C. to 40° C. during addition. At this stage the mixture included 6 volumes of ethyl acetate, 10 volumes of water, and 13 volumes of n-heptane for each volume of crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate. The reaction mixture was stirred for at least 15 min while maintaining an internal temperature of 30° C. to 40° C. A slurry (triphasic mixture: organic layer, aqueous layer and solids) gradually forms. When stirred, the mixture appeared hazy (organic/aqueous emulsion). It is recommended to temporarily stop agitation to allow the layers to separate (fast separation) to better observe the formation of solids. An additional amount of n-heptane (99%) was charged to the reaction mixture over a minimum of 1 h while maintaining an internal temperature of 30° C. to 40° C. during the addition. The slurry (triphasic mixture: organic layer, aqueous layer and solids) became thicker during the addition of the n-hexane. The slurry was then cooled to an internal temperature of 0° C. to 10° C. over a minimum period of 3 h at a target cooling rate of −10° C. per h. The slurry was then stirred for a minimum 1 h while maintaining an internal temperature of 0° C. to 10° C. (target 5° C.). The solids were filter washed with n-heptane, EtOAc, and water, and dried to provide crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1).

Example 3

X-Ray Powder Diffraction (XPRD) Analysis

X-ray powder diffraction (XPRD) analysis was performed using a Panalytical X-Pert Powder XPRD (Malvem Panalytical Ltd.) on a Si zero-background holder. The 2θ position was calibrated against a Panalytical Si standard disc. The X-ray wavelength was Kα2/Kα1 (1.540598 Å/1.544425 Å) at a 0.5 intensity ratio. The X-ray tube was set at an output voltage of 45 kV and a current of 40 mA. A ⅛° fixed divergence slit was used and the diffraction patterns were obtained from 3° to 40° (°2θ) in a continuous scan mode using a step size of 0.01310 (2θ) and a scan speed of 0.145 deg/min.

Representative XPRD diffraction patterns of crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1) are shown in FIGS. 1 and 3. FIG. 1 shows an XPRD pattern of the as crystallized anhydrate (1), and FIG. 3 compares XRPD patterns of crystalline anhydrate (1) be before and after milling.

Example 4

Differential Scanning Calorimetry

Differential scanning calorimetry was performed using a TA Instruments Q2000 DSC and calibrated with an indium reference standard. Samples were loaded into crimped aluminum pans. Following equilibration at 25° C., the samples were heated under a nitrogen (N$_2$) atmosphere at a rate of 10° C./min to a final temperature of 200° C. DSC curves are shown in FIGS. 2 and 4 and reflect a melting point for crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1) of 123.99° C. FIG. 2 shows a DSC curve before milling and FIG. 4 shows a DSC curve after milling.

Example 5

Thermogravimetric Analysis

Thermogravimetric analysis was performed using a TA Instruments Q500 TGA calibrated using a nickel reference standard. Samples were placed in an open platinum pan and after equilibrating at 35° C., the samples were heated under a nitrogen (N$_2$) atmosphere at a rate of 10° C./min to a final temperature of 200° C. TGA curves for crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate are shown in FIGS. 2 and 4 show a weight loss of 9.7% between 125° C. to 150° C. The weight loss form 30° C. to 125° C. was 0.77%. FIG. 2 shows a TGA curve before milling and FIG. 4 shows a TGA curve after milling.

The TGA thermogram shows that the crystalline anhydrate (1) did not undergo any appreciable weight loss prior to melting, which indicated that the crystalline form was anhydrous.

Example 6

Dynamic Vapor Sorption

The hygroscopicity of crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate (1) was evaluated during one vapor sorption/desorption cycle using a SMS DVS Intrinsic from Surface Measurement Systems set at 25° C., with a nitrogen ($N_2$) gas flow rate of 200 mL/min, a dm/dt of 0.02%/min and a minimum dm/dt stability duration of 10 min.

Samples (10 mg to 20 mg) were first dried at 25° C. for 180 min under a nitrogen atmosphere. The samples were considered equilibrated with the weight change during a 2-min interval was less than 0.01%. To evaluate the DVS the samples were exposed to a humidity cycle ramped/de-ramped from 5% RH to 95% RH at 10% RH intervals. At each humidity interval, the samples were equilibrated as determined by a less than 0.01% weight change during 5 min. The results are shown in FIG. 5.

The reversibility of the DVS isotherm demonstrates that the crystalline form does not change during water absorption/desorption.

Example 7

Jet Milling

Crystalline anhydrate (1) was jet milled to obtain a uniform particle size distribution centered at a about 8.6 μm. An Alpine 50AS (PDS-PL-JM-01) Jet Mill (Hosokawa Alpine) was used to prepare the formulation. The injector gas pressure was 4.0 Bar and the grinding gas pressure was 3.5 Bar. Five (5) gm of crystalline anhydrate (1) was gradually added to the jet mill and collected. The milled product was stored at a temperature from 2° C. to 8° C.

XRPD patterns of crystalline anhydrate (1) before and after jet-milling are compared in FIG. 3 and show that the crystalline form before and after jet-milling was the same. TGA and DSC scans of the jet-milled material are shown in FIG. 4 and were similar to those for the un-milled material shown in FIG. 2.

Example 8

Aqueous Formulation

An aqueous formulation of crystalline anhydrate (1) was prepared by suspending 100 mg crystalline anhydrate (1) in 100 mL of an aqueous solution containing 0.25 wt % Tween® 80, 10 wt % PEG 400, 0.5 wt % methylcellulose (400 cps), and a pH 3.0 citrate buffer. The suspension was sonicated and equilibrated for 24 hours at 25° C. before filtering out the crystalline anhydrate (1).

XRPD patterns of jet-milled material (Example 7) and the material obtained from the filtered aqueous suspension are compared in FIG. 6. The similarity of the XRPD patterns demonstrated that crystalline anhydrous (1) was stable in an aqueous suspension at 25° C.

It should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. The compound, crystalline ethyl 3-(((((1R,2S,5R)-2-carbamoyl-7-oxo-1,6-diazabicyclo[3.2.1]octan-6-yl)oxy)sulfonyl)oxy)-2,2-dimethylpropanoate anhydrate characterized by an X-ray powder diffraction (XRPD) pattern having characteristic scattering angles (2θ) at least at 3.16°±0.2°, 6.37°±0.2°, 5.38°±0.2°, and 17.35°±0.2° at a Kα2/Kα1 (0.5) wavelength.

2. The compound of claim 1, characterized by an XRPD pattern having characteristic scattering angles (2θ) at least at 3.16°±0.2°, 6.37°±0.2°, 5.38°±0.2°, 15.77°±0.2°, and 17.35°±0.2° at a Kα2/Kα1 (0.5) wavelength.

3. The compound of claim 1, characterized by an XRPD pattern having characteristic scattering angles (2θ) at least at 3.16°±0.2°, 6.37°±0.2°, 5.38°±0.2°, 12.75°±0.2°, 15.77°±0.2°, 17.35°±0.2°, 25.68°±0.2°, and 27.13°±0.2° at a Kα2/Kα1 (0.5) wavelength.

4. The compound of claim 1, wherein the compound exhibits a melting point from 123.0° C. to 127.0° C. as determined by differential scanning calorimetry.

5. A pharmaceutical composition comprising the compound of claim 1 and a pharmaceutically acceptable vehicle, wherein the pharmaceutical composition comprises an aqueous suspension.

6. The compound of claim 1, characterized by an XRPD pattern having characteristic scattering angles (2θ) at least at 3.16°±0.1°, 6.37°±0.1°, 5.38°±0.1°, and 17.35°±0.1° at a Kα2/Kα1 (0.5) wavelength.

7. The compound of claim 1, characterized by an XRPD pattern having characteristic scattering angles (2θ) at least at 3.16°±0.1°, 6.37°±0.1°, 5.38°±0.1°, 15.77°±0.1°, and 17.35°±0.1° at a Kα2/Kα1 (0.5) wavelength.

8. The compound of claim 1, characterized by an XRPD pattern having characteristic scattering angles (2θ) at least at 3.16°±0.1°, 6.37°±0.1°, 5.38°±0.1°, 12.75°±0.1°, 15.77°±0.1°, 17.35°±0.1°, 25.68°±0.1°, and 27.13°±0.1° at a Kα2/Kα1 (0.5) wavelength.

9. The compound of claim 1, wherein the compound exhibits a melting point from 124.2° C., or from 123.9° C. as determined by differential scanning calorimetry.

10. The compound of claim 1, wherein the compound exhibits a reversible moisture absorption over a range of humidity from 0% RH to 95% RH with a maximum increase in mass of 3 wt % at 25° C./95% RH as determined using dynamic vapor sorption.

11. The compound of claim 1, wherein the compound is storage stable during storage at 25° C./60% RH for 4 weeks, wherein storage stable means that the melting point, the weight loss, and the moisture absorption before and after storage at 25° C./60% RH are within less than 5%.

12. The compound of claim 1, wherein the compound exhibits a weight loss from 7.2% to 9.2% over a temperature range from 125° C. to 150° C., and no appreciable weight loss over the range from 30° C. to 125° C. as determined by thermogravimetric analysis (TGA).

* * * * *